United States Patent [19]

Bartrolí et al.

[11] Patent Number: 5,134,151
[45] Date of Patent: Jul. 28, 1992

[54] 2-PICOLYLAMINE DERIVATIVES

[75] Inventors: Javier Bartrolí; Manuel Anguita; Elena Carceller, all of Barcelona, Spain

[73] Assignee: J. Uriach & Cia, Barcelona, Spain

[21] Appl. No.: 487,476

[22] Filed: Mar. 2, 1990

[30] Foreign Application Priority Data

Mar. 2, 1989 [ES] Spain ................................ 8900754

[51] Int. Cl.$^5$ .................. C07D 213/36; C07D 213/53; C07D 213/54; A61K 31/44
[52] U.S. Cl. ..................................... 514/357; 546/329; 546/348
[58] Field of Search ................. 546/348, 329; 514/357

[56] References Cited

FOREIGN PATENT DOCUMENTS

| | | | |
|---|---|---|---|
| 0138559 | 4/1985 | European Pat. Off. | 546/22 |
| 0147768 | 7/1985 | European Pat. Off. | 546/22 |
| 0157609 | 10/1985 | European Pat. Off. | 546/22 |
| 0178261 | 4/1986 | European Pat. Off. | 546/23 |
| 0210804 | 2/1987 | European Pat. Off. | 548/112 |
| 0238202 | 9/1987 | European Pat. Off. | 546/22 |
| 0312040 | 10/1987 | European Pat. Off. | 546/283 |
| 0312041 | 10/1987 | European Pat. Off. | 546/268 |
| 0251827 | 1/1988 | European Pat. Off. | 546/283 |
| 0254540 | 1/1988 | European Pat. Off. | 568/11 |
| 57-165394 | 12/1982 | Japan | 562/11 |
| 58-35116 | 1/1983 | Japan | 546/22 |
| 61-93191 | 12/1986 | Japan | 548/112 |
| WO8601507 | 3/1986 | PCT Int'l Appl. | 546/329 |

*Primary Examiner*—Alan L. Rotman
*Attorney, Agent, or Firm*—Rothwell, Figg, Ernst & Kurz

[57] ABSTRACT

The present invention relates to novel 2-picolylamine derivatives of general formula I

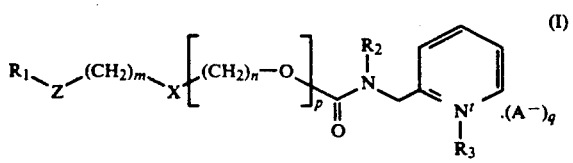

wherein $R_1$ represents an alkyl or phenylalkyl radical; $R_2$ is hydrogen, $C_1$-$C_4$ acyl or $C_1$-$C_4$ alkoxycarbonyl; $R_3$ is either an electron pair, in which case t means nothing and q is 0, or $R_3$ is hydrogen or $C_1$-$C_4$, in which case t is (+) and q=1; Z is oxygen or an aminocarboniloxy group; X is O or S; m and n are 2-6; p is 0-3; $A^-$ is a pharmaceutically acceptable ion. These compounds are PAF antagonists and, consequently, useful in the treatment of the diseases in which this substance is involved.

19 Claims, No Drawings

2-PICOLYLAMINE DERIVATIVES

SUMMARY OF THE INVENTION

The present invention relates to new 2-picolylamine derivatives with a potent antagonist activity of the platelet activating factor (PAF), together with a process for their preparation. The invention also relates to the pharmaceutical preparations which contain these compounds and their use in the treatment of diseases in which PAF is involved, such as allergic and bronchial asthma, platelet aggregation disorders, septic shock, hypertension, etc.

The platelet activating factor (PAF) or (1-O-alkyl-2-acetyl-sn-glyceryl-3-phosphorylcholine), also called acetyl glyceryl ether phosphorylcholine (AGEPC) or PAF-acether is a natural phospholipid synthesized by different cells (basophiles, macrophages, neutrophiles, platelets) and tissues (heart, lung and kidney) of the organism (Roubin et al. in "Lymphokines" Ed. E. Pick, Acad. Press. New York, p. 249, 1983; Vargaftig et al, Ann. N.Y. Acad. Sci., 1981, 370, 119; Pinckard et al., Int. Arch. Allergy Appl. Immun., 1981, 66, 127).

PAF was described for the first time as a potent platelet aggregating agent (Benveniste, et al., J. Exp. Med., 1972, 136) and later it was demonstrated to have other biological activities in vivo, such as peripheral vasodilatation, increase of the vascular permeability, induction of bronchoconstriction and hyperreactivity of the respiratory tract (Mazzoni, et al. J. Physiol. 1985, 365, 107P). PAF also produces immediate hypotension followed by pulmonary and renal hypertension in rats (Blank, et al., Biochem. Biophis. Res. Commun., 1979, 90, 1194), guinea pigs (Feuerstein, et al., Circul. Shock, 1984, 13, 255), rabbits (Muirhead, et al., Hypertension, 1981, 3, 107) and dogs (Otsuka, et al., Prostaglandins Leukotrienes Med., 1985, 19, 25), and it has been rated as the most potent ulcerogenic agent described until now.

Consequently, PAF is a mediator that is implicated in a large set of pathological processes such as asthma, septic shock, transplant rejection, thrombosis, ulceration, inflammation and renal diseases.

Even though its mechanism of action is still not known with precision, some studies show that the biological activities of PAF involve the existence of a specific receptor. Recently, the isolation of one of these receptors from human platelets has been achieved and it has been identified as a protein with a molecular weight of 160.000 daltons (Nishihira et al., Tohoku J. Exp. Med., 1985, 147, 145). On the other hand, the capacity to inhibit the binding of $^3$H-PAF to their receptors is well correlated with the amount of PAF needed to cause the in vitro and in vivo observed effects. These facts indicate that the compounds that act as specific antagonists of PAF could result of interest for the treatment of all those pathological processes related directly or indirectly with PAF.

According to the above mentioned activities, PAF antagonists have been investigated with the aim of developing new types of anti-shock, anti-inflammatory and anti-asthma agents. In particular, analogues of natural PAF's have been investigated in an attempt to find such PAF antagonists. These compounds are disclosed in patents EP 138559, JP 57/165394, JP 58/35116, JP 61 93191, EP 178261, and EP 210804, among others. Some non-phosphate glycerol derivatives have been shown to posess PAF antagonist activity, like, for example, those disclosed in patents EP 147768, and EP 254540. Patents EP 157609, EP 238202, EP 251827, EP 312041 and EP 312040 disclose compounds having the substituent depicted in FIG. 1, which also appears in the compounds of the present invention.

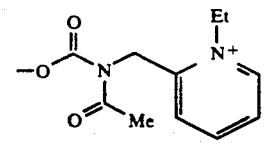

FIG. 1

The compounds disclosed in the above-mentioned patents, however, are unsatisfactory for one or more of the following reasons: they lack sufficient PAF antagonist activity; they have short half-lives; their biological utilization is inadequate; their syntheses is too tedious.

The closest prior art, from the structural point of view, to the compounds of the present invention is believed to be the compounds disclosed in WO 86/01507, which relates to cyclimmonium salts with PAF antagonist action, of formula,

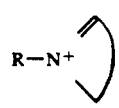

FIG. 2 wherein R represents a linear radical of diverse nature, but where the cyclic ring is always linked to the radical R through the quaternary nitrogen, as shown in FIG. 2. On the contrary, the compounds of the present invention not only are structurally different, but additionally, they show a remarkably more potent PAF-antagonist activity. An additional advantage of the compounds of the present invention in relation to the above-mentioned compounds is that they can be easily obtained by a straightforward, five step synthesis from cheap, commercially available glycols.

DETAILED DESCRIPTION OF THE INVENTION

The compounds to which the present invention relates may be represented by the formula (I):

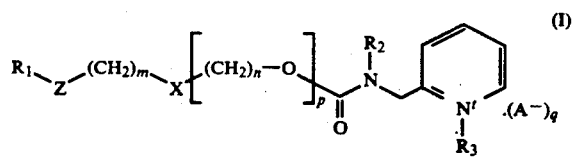

in which:
- $R_1$ represents a $C_{10}$-$C_{24}$ alkyl, alkenyl or alkynyl group, a tert-butyl group, an aryl-$C_1$-$C_{12}$ alkyl group or a cyclohexyl-$C_1$-$C_{12}$ alkyl group,
- $R_2$ represents hydrogen, or a —C(=O)$R_4$ group, where $R_4$ represents a $C_1$-$C_6$ alkyl group or $C_1$-$C_6$ alkoxy;
- Z is —O—, —C(=O)O— or —NR$_5$C(=O)O—, where R$_5$ is hydrogen, $C_1$-$C_4$ alkyl, or $C_1$-$C_4$ acyl;
- X is —O— or —S—;
- m and n are 2, 3, 4, 5, or 6 independently;
- p is 0, 1, 2 or 3;
- q is 0 or 1;
- t is (+) when q=1, and t has no meaning when q=0;

$R_3$ is hydrogen or $C_1$-$C_6$-alkyl when $q=1$, and it is an electron pair when $q=0$;

$A^-$ represents a pharmaceutically acceptable anion.

The invention also provides the use for the manufacture of a medicament for the treatment or prophylaxis of PAF-mediated illnesses in an animal, especially a mammal, which may be a human being, of at least one compound of formula (I)

The invention still further provides a pharmaceutical composition comprising an effective amount of at least one compound of formula (I) in admixture with a pharmaceutically acceptable carrier or diluent.

The invention also provides processes for preparing the compounds of the present invention, which in general terms comprise:

(a) reacting a compound of formula (II):

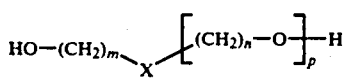
(II)

[in which X, m, n and p are as defined above] with a compound of formula (III)

 (III)

[in which $R_1$ is as defined above, and W is halide, p-toluenesulfonyloxy, methylsulfonyloxy, —N=C=O, —OC(=O)Cl, or —C(=O)Cl] to give a compound of formula (IV)

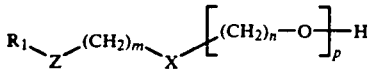
(IV)

[in which X, Z, $R_1$, m, n and p are as defined above] and reacting said compound of formula (IV) with a compound of formula (V)

$Y'C(=O)Y''$ (V)

[in which Y' and Y'' are good leaving groups] to give a compound of formula (VI)

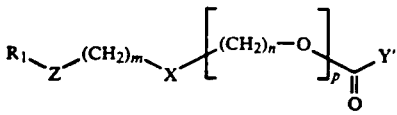
(VI)

[in which X, Z, $R_1$, Y', m, n and p are as defined above] and reacting said compound of formula (VI) with 2-aminomethylpyridine to afford a compound of formula (Ia)

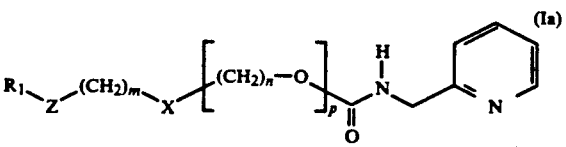
(Ia)

[in which X, Z, $R_1$, m, n and p are as defined above] and optionally reacting said compound of formula (Ia) with a compound of formula (VII)

$ClC(=O)R_4$ (VII)

[in which $R_4$ is as defined above] to give a compound of formula (Ib)

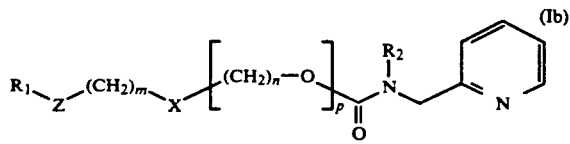
(Ib)

[in which X, Z, $R_1$, $R_2$, m, n and p are as defined above, but $R_2$ is different from hydrogen] and optionally reacting said compound (Ib) with a compound of formula (VIII)

$R_3Y'''$ (VIII)

[in which $R_3$ is as defined above and Y''' is halide, methyl sulfonate or p-toluenesulfonate] to afford a compound of formula (Id)

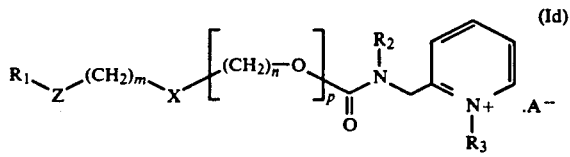
(Id)

[in which X, Z, $R_1$, $R_2$, $R_3$, A, m, n and p are as defined above, but $R_2$ is different from hydrogen]; or (b) optionally reacting a compound of formula (Ia) with a compound of formula (VIII) to give a compound of formula (Ic)

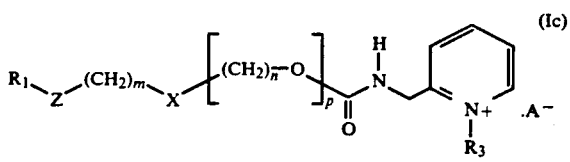
(Ic)

[in which X, Z, $R_1$, $R_3$, A, m, n and p are as defined above].

(c) optionally changing anion A by another pharmaceutically acceptable anion by means of ion-exchange chromatography or selective salt precipitation.

In the compounds of the present invention, where $R_1$ represents an alkyl group, this may be a straight or branched chain alkyl group containing from 10 to 24 carbon atoms, and examples include the n-decyl, n-undecyl, n-dodecyl, n-tridecyl, n-tetradecyl, n-pentadecyl, n-hexadecyl, n-heptadecyl, n-octadecyl, n-nonadecyl, n-eicosenyl groups, or a tert-butyl group, or 4-phenylbutyl, 3-phenylpropyl, 2-phenylethyl, phenylmethyl, 5-cyclohexylpentyl, 4-cyclohexylbutyl, 3-cyclohexylpropyl, 2-cyclohexylethyl and cyclohexylmethyl groups, of which the n-tetradecyl, n-pentadecyl, n-hexadecyl, n-heptadecyl, n-octadecyl, n-nonadecyl, 3-phenylpropyl and cyclohexylmethyl groups are preferred, and the n-pentadecyl, n-hexadecyl, n-heptadecyl, n-octadecyl groups are most preferred.

Where $R_2$ represents hydrogen or a group of formula —C(=O)$R_4$, and $R_4$ represents a $C_1$-$C_6$ alkyl group or $C_1$-$C_6$ alkoxy group, $R_4$ may be a straight or branched chain alkyl or alkoxy group containing 1 to 6 carbon atoms, and examples include methyl, ethyl, n-propyl, iso-propyl, n-butyl, iso-butyl, tert-butyl, n-pentyl, iso-pentyl, neo-pentyl, n-hexyl, methoxy, ethoxy, n-propoxy, iso-propoxy, iso-butoxy, tert-butoxy, n-pentoxy, iso-pentoxy and n-hexoxy, of which the methyl and ethoxy groups are more preferred, and the methyl group is most preferred.

Where $R_3$ represents hydrogen or a $C_1$-$C_6$ alkyl group this may be a straight or branched chain alkyl group containing 1 to 6 carbon atoms, and examples include methyl, ethyl, n-propyl, iso-propyl, n-butyl, iso-butyl, tert-butyl, n-pentyl, iso-pentyl, neo-pentyl, n-hexyl, of which ethyl is the most preferred.

Where Z represents a group of formula —O—, —C(=O)O—, or —NR$_5$C(=O)O—, where $R_5$ is hydrogen, $C_1$-$C_4$ alkyl or $C_1$-$C_4$ acyl, the groups —O— and —NHC(=O)O— are most preferred.

Where m and n are 2, 3, 4, 5, or 6 independently, and p is 0, 1, 2 or 3, the combinations m=n=2, p=1; m=n=2, p=2; and m=5 or 6, n=p=0 are preferred, and the combination m=n=2, p=1 is the most preferred.

Where q is 0 or 1 and t is (+) or means nothing, q=1 and t=(+) is most preferred.

Where A- represents a pharmaceutically acceptable anion this may be fluoride, chloride, bromide, iodide, methylsulfonate, p-toluenesulfonate, maleate, fumarate, nitrate, sulfate or oxalate, of which chloride, iodide, p-toluenesulfonate, methylsulfonate, and nitrate are more preferred, and iodide and chloride are most preferred.

The compounds of the present invention can exist in the form of various optical isomers and stereisomers because of the existence of asymmetric carbons in the molecule. The optical isomers can be resolved using conventional techniques of optical resolution to give optically active compounds. The diastereomers and geometrical isomers can be resolved using conventional techniques for separation such as recrystallization or chromatography. The present invention covers both the individual isomers and mixtures (e.g. racemic mixtures) thereof, whether as obtained by the synthesis reaction or by mixing.

Examples of specific compounds of the invention are given in the following formulae, in which the number indicates the number of the example in which their preparation is described.

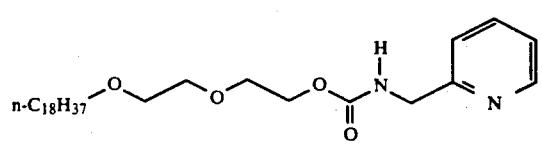

1

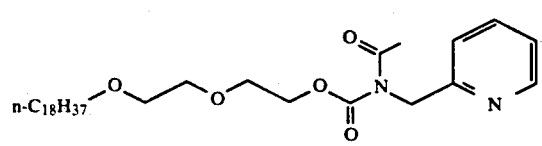

2

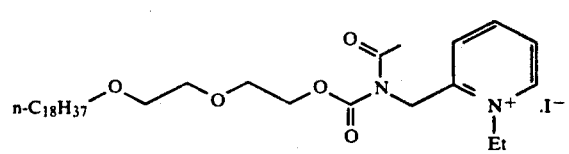

3

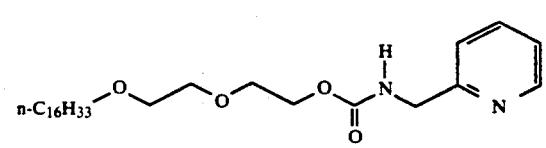

4

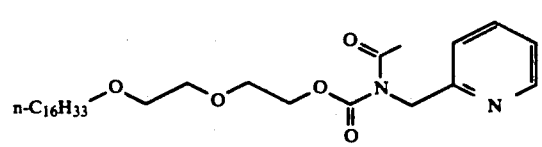

5

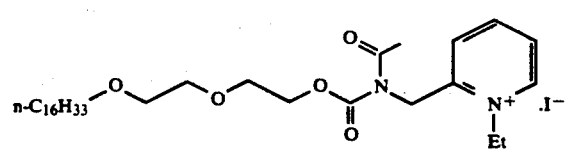

6

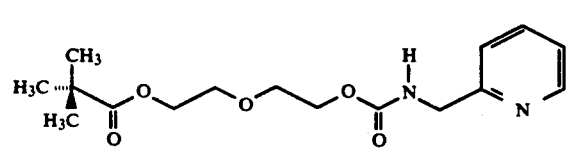

7

8
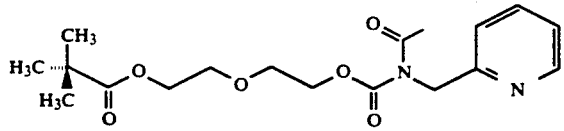
9
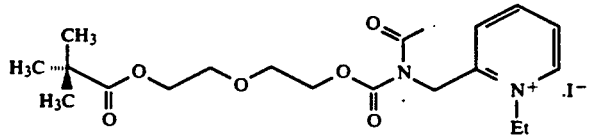
10
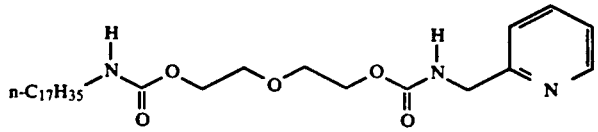
11
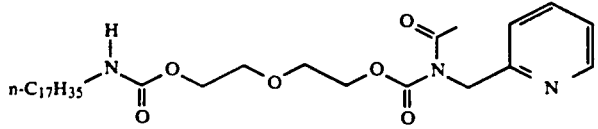
12
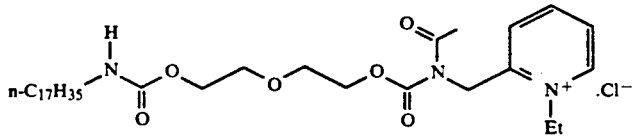
13
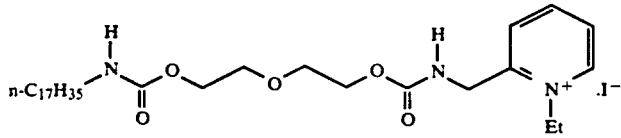
14
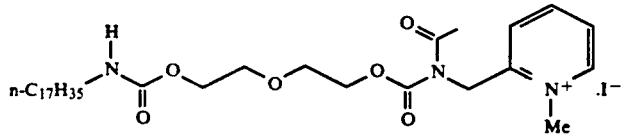
15
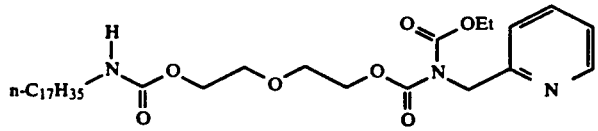
16
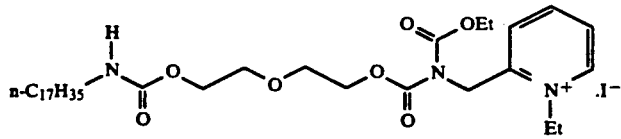
17
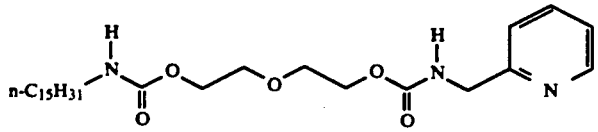

-continued
18
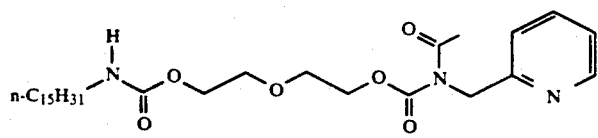
19
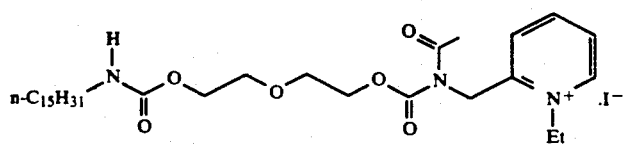
20
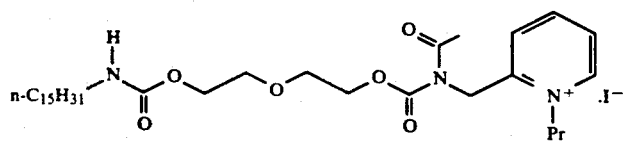
21
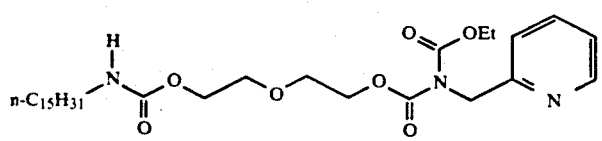
22
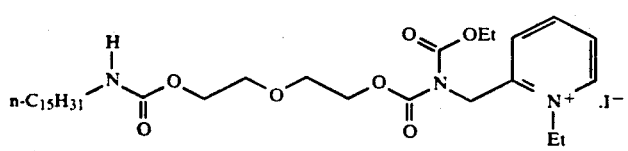
23
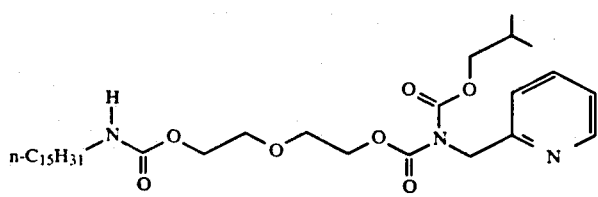
24
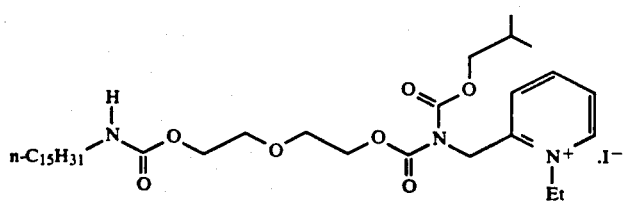
25
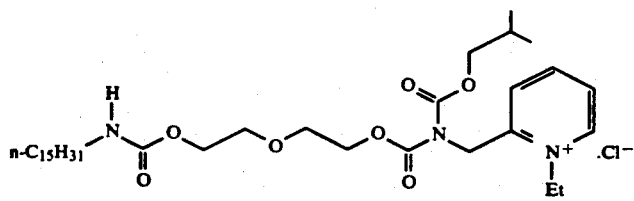
26
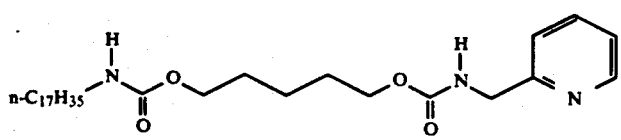

27
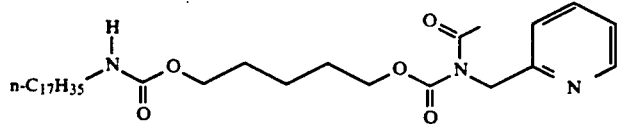
28
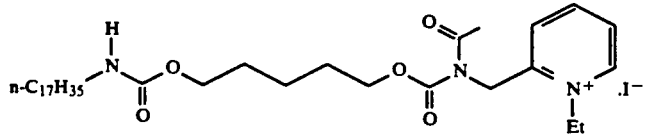
29
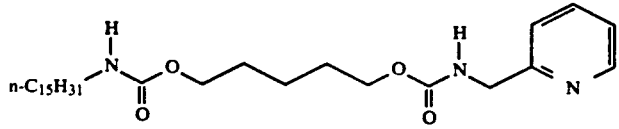
30
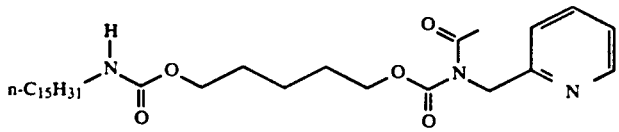
31
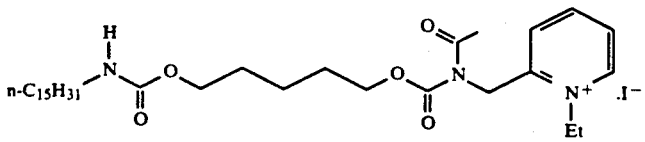
32
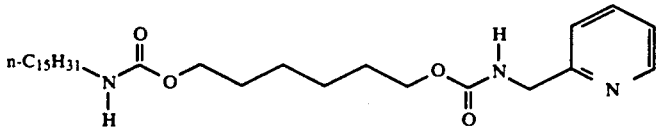
33
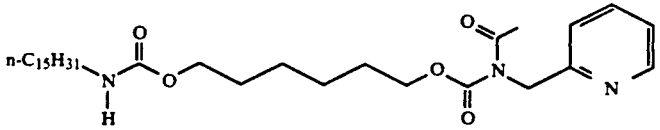
34
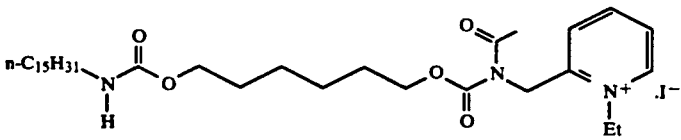
35
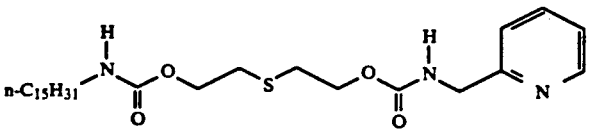
36
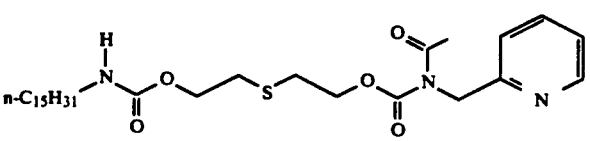

-continued
37
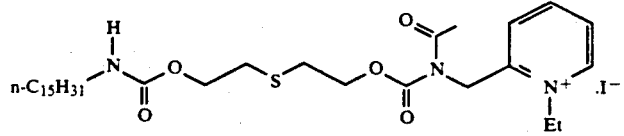
38
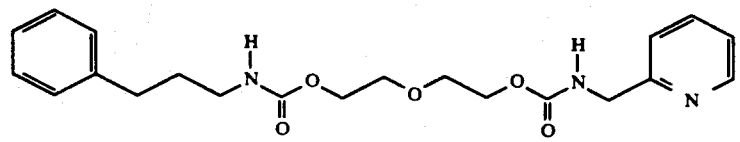
39
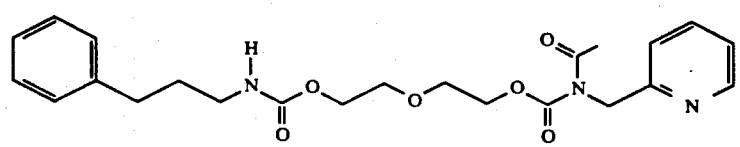
40
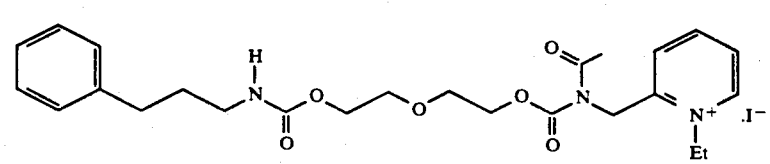
41
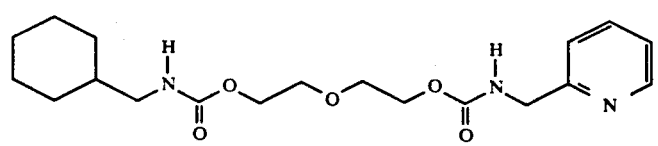
42
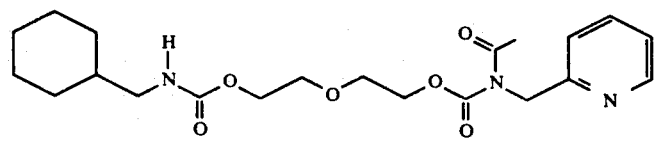
43
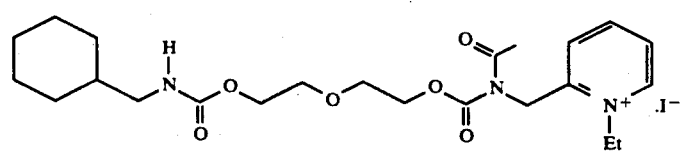
44
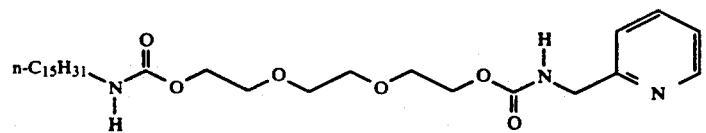
45
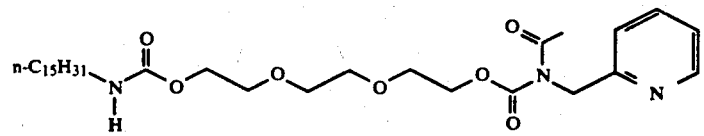
46
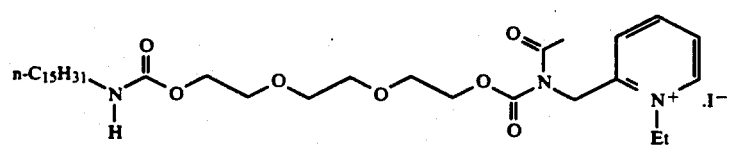

47
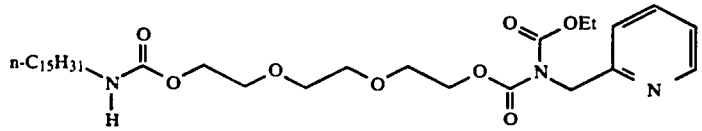
48
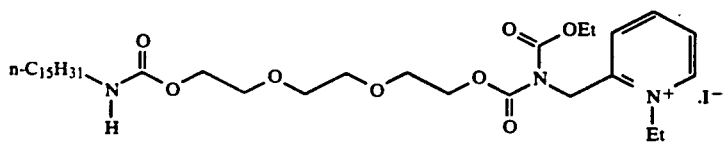
49
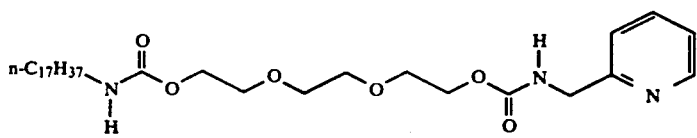
50
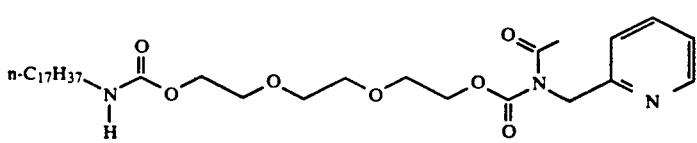
51
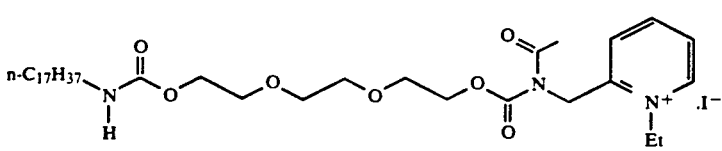
52
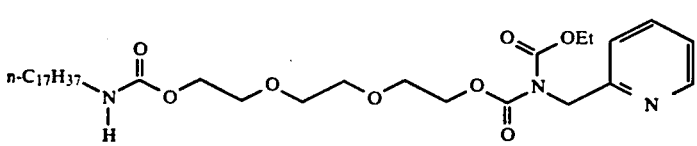
53
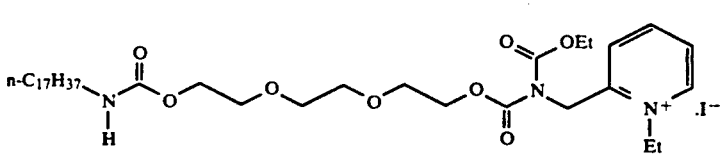
54
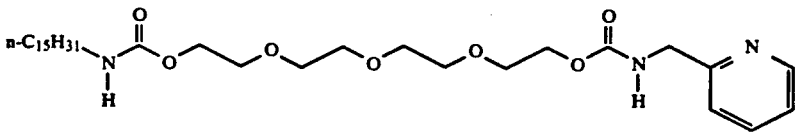
55
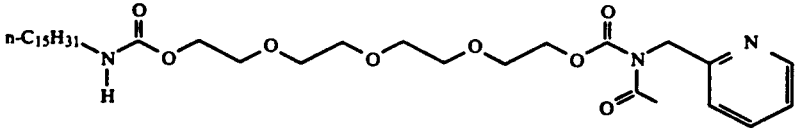
56
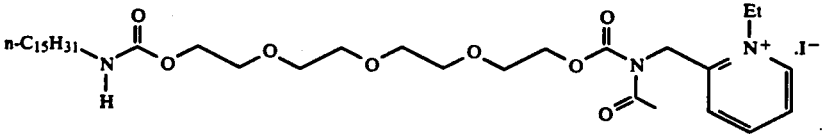

57 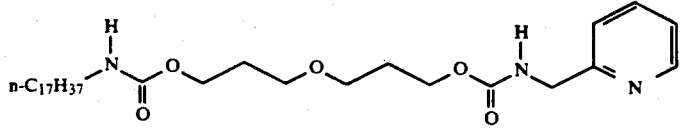
58 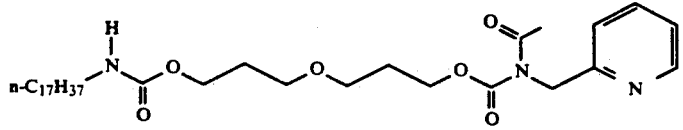
59 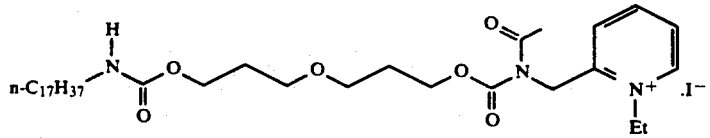
60 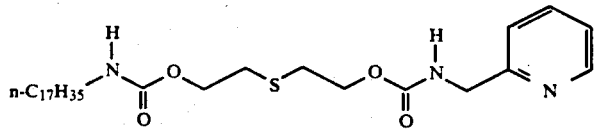
61 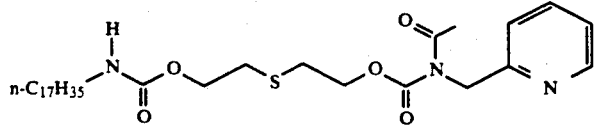
62 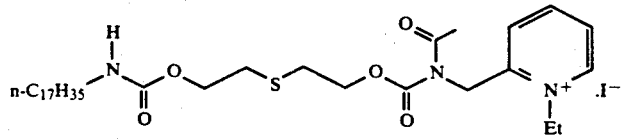
63 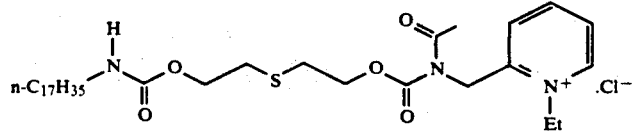
64 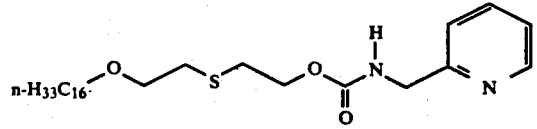
65 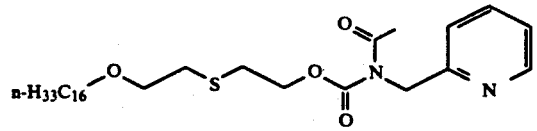
66 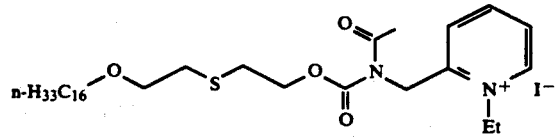

-continued

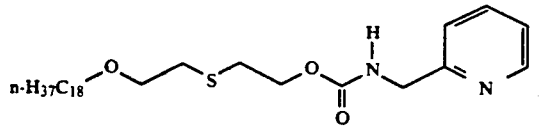

67

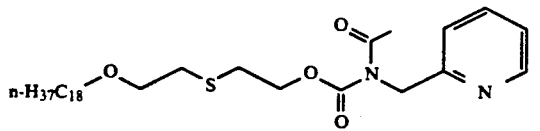

68

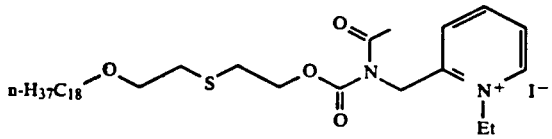

69

Of the compounds listed above, the following are preferred, that is to say Compounds No. 3, 6, 9, 12, 13, 14, 16, 19, 20, 22, 24, 25, 28, 31, 34, 37, 40, 43, 46, 48, 51, 53, 56, 59, 62, 63, 66 and 67. The are more preferred, that is Compounds No. 3, 6, 12, 19, 22, 28, 31, 37, 46, 62, 63, 66 and 67.

The most preferred compounds are:

No. 3: 2-(N-Acetyl-N-((2-(2-octadecyloxyethoxy)ethoxy)carbonyl) aminomethyl)-1-ethylpyridinium iodide;

No. 19: 2-(N-Acetyl-N-((2-(2-(pentadecylcarbamoyloxy)ethoxy) ethoxy)carbonyl)aminomethyl)-1-ethylpyridinium iodide.

No. 31: 2-(N-Acetyl-N-((5-(pentadecylcarbamoyloxy)-pentoxy) carbonyl) aminomethyl)-1-ethylpyridinium iodide.

No. 37: 2-(N-Acetyl-N-((2-(2-(pentadecylcarbamoyloxy) ethylthio) ethoxy) carbonyl) aminomethyl)-1-ethylpyridinium iodide.

No. 46: 2-(N-Acetyl-N-((2-(2-(2-(pentadecylcarbamoyloxy) ethoxy) ethoxy) ethoxy) carbonyl)aminomethyl)-1-ethylpyridinium iodide.

No. 62: 2-(N-Acetyl-N-((2-(2-(heptadecylcarbamoyloxy) ethylthio) ethoxy) carbonyl) aminomethyl)-1-ethylpyridinium iodide.

No. 63: 2-(N-Acetyl-N-((2-(2-(heptadecylcarbamoyloxy) ethylthio) ethoxy) carbonyl) aminomethyl)-1-ethylpyridinium chloride.

No. 66: 2-(N-Acetyl-N-((2-(2-hexadecyloxyethylthio) ethoxy) carbonyl) aminomethyl)-1-ethylpyridinium iodide.

No. 69: 2-(N-Acetyl-N-((2-(2-octadecyloxyethylthio) ethoxy) carbonyl) aminomethyl)-1-ethylpyridinium iodide.

The compounds of the present invention may be prepared by a variety of methods known for the preparation of this type of compounds. In general, the precise details of the method chosen for their preparation will vary depending on the nature of the compound. Scheme I shows the general strategy for their preparation According to that scheme, in the first step (step A) diol II is reacted with a compound $W-R_1$, wherein W is either a $-N=C=O$, $-C(=O)Cl$ or a $-OC(=O)Cl$ group or a leaving group such as halogen (Cl, Br, I) or aryl or alkyl sulfonate ($CH_3SO_3-$, $p-CH_3C_6H_4SO_3-$). When W is $-N=C=O$, $-C(=O)Cl$ or $-OC(=O)Cl$, then Z is, respectively, $-NHC(=O)O-$, $-C(=O)O-$ or $-OC(=O)O-$ and the corresponding step A is carried out in a solvent. There is no particular restriction on the nature of the solvent to be employed, provided that it has no adverse effect on the reaction or on the reagents involved. Examples of suitable solvents include: hydrocarbons, especially aromatic hydrocarbons, such as toluene; halogenated hydrocarbons, especially halogenated aliphatic hydrocarbons, such as dichloromethane and chloroform; and ether, such as tetrahydrofuran and diethyl ether. The reaction is carried out in the presence of a base that can be used as a solvent. Although there is no particular restriction in the base used, it is preferred to perform the reaction using a tertiary amine such as triethylamine or pyridine. The reaction can take place over a wide range of temperatures, and the precise reaction temperature is not critical to the invention. In general, we find it convenient to carry out the reaction at a temperature from 0° C. to 100° C., but more conveniently between 0° and 50° C. The time required for the reaction may also vary widely, depending on many factors, notably the reaction temperature and the nature of the reagents. However, provided that the raction is effected under the preferred conditions outlined above, a period of from 30 minutes to 24 hours will usually suffice. Although the reaction is clean, if desired, the product IV can be purified by flash chromatography.

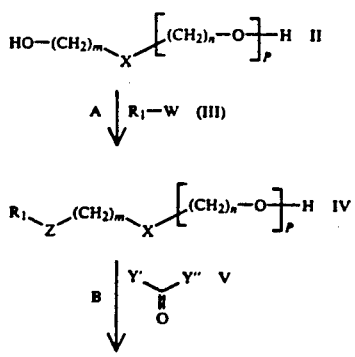

-continued

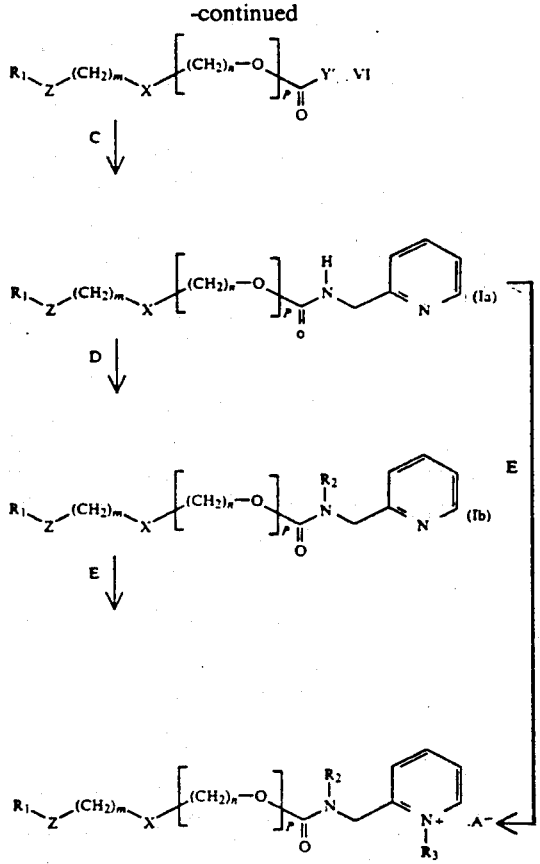

Ic: $R_2 = H$
Id: $R_2 = C(=O)R_4$

In the case in which Z is an oxygen atom, the step A is carried out preparing first the alkoxide of the compound II and using a reagent W-R$_1$, wherein W is a leaving group. The formation of the alkoxide is performed by the treatment of II with a strong base, such as sodium hydride or butyl lithium, in a solvent that does not interfere with the reagents. Examples of suitable solvents include N,N-dimethylformamide or tetrahydrofuran. The reaction of the alkoxide formation is carried out between 0° and 80° C., during a period of time from 10 minutes and 2 hours. In the second phase of the reaction, the reagent W-R$_1$ is added and, at a similar temperature margin, is allowed to react during a period of time from 1 to 24 hours, depending on the nature of W and the temperature used. The desired compound is isolated by conventional methods but, if desired, can be purified by flash chromatography.

In the second step (step B), the alcohol IV is allowed to react with a compound V, one of the so-called phosgene equivalents, that is to say, a doubly activated carbonyl group. In the compound V, the groups Y' and Y''' are leaving groups and can be identical (Cl, imidazole, etc.) or different. Although in principle any phosgene equivalent described in the literature could be employed, we have found that phenyl chlorocarbonate (V, Y''=Cl, Y'=OPh) is an excellent reagent to carry out this reaction, due to its convenient handling, and low cost. The reaction is carried out in a solvent in the presence of a proton scavenger base. There is no particular restriction on the nature of the solvent to be employed, provided that it has no adverse effect on the reaction or on the reagents involved. Examples of suitable solvents include: hydrocarbons, especially aromatic hydrocarbons, such as toluene; halogenated hydrocarbons, especially halogenated aliphatic hydrocarbons, such as dichloromethane and chloroform; and ethers, such as tetrahydrofuran and diethyl ether. Neither any particular restriction exists with respect to the base provided that it does not interfere with other parts of the molecule. It is preferred to use an amine, such as triethylamine or pyridine. The reaction can take place over a wide range of temperatures, and the precise reaction temperature is not critical to the invention. In general, we find it convenient to carry out the reaction at a temperature from 0° to 100° C., but temperatures from 0° to 50° C. are preferred. The time required for the reaction may also vary widely, depending on many factors, notably the reaction temperature and the nature of the reagents. However, provided that the reaction is effected under the preferred conditions outlined above, a period of from 30 min to 24 hours will usually suffice. The reaction is clean and usually purification of the product it is not necessary. However, if desired, product VI can be purified by flash chromatography.

In the step C compound VI (obtained in step B) is converted into the carbamate (Ia) by reaction with 2-picolylamine. The reaction can be performed in a solvent at a temperature and a period of time similar to those described in step B. The crude reaction mixture is washed, in this case, with an alkaline aqueous solution in order to remove the phenol produced during the reaction. The product obtained (Ia) can be purified by conventional methods such as flash chromatography.

Step D involves the derivatization of the carbamic nitrogen of compound (Ia) to give the compound (Ib). The reaction involves the use of a reagent of formula $R_4C(=O)Cl$ where $R_4$ has the previous meaning. The reaction is preferably effected in an inert solvent. There is no particular restriction on the nature of the solvent to be employed, provided that it has no adverse effect on the reaction or on the reagents involved. Examples of suitable solvents include halogenated hydrocarbons, especially halogenated aliphatic hydrocarbons, such as dichloromethane and chloroform. On the other hand, the reaction can be done in the presence of a proton scavenger amine, such as triethylamine. The use of the amine is optional because the pyridinic ring has a basic nitrogen itself. The reaction can take place over a wide range of temperatures, and the precise reaction temperature is not critical to the invention. In general, we find it convenient to carry out the reaction at a temperature from 0° C. to the boiling point of the solvent used, but a temperature near the room temperature will generally suffice The time required for the reaction may also vary widely, depending on many factors, notably the reaction temperature and the nature of the reagents. However, provided that the raction is effected under the preferred conditions outlined above, a period of from 2 to 72 hours is usually enough. Once the reaction is complete, the desired product, of formula (Ib), can be isolated and purified by conventional methods such as flash chromatography.

Step F involves the transformation of a compound (Ia) or (Ib) into a compound (Ic) or (Id), respectively. The reaction is carried out between the starting material and a reagent of formula R$_3$A wherein R$_3$ is a lower alkyl group. The reaction can be performed without solvent in the case where R$_3$A is liquid and non-volatile, or in the presence of a solvent when R$_3$A is solid or very volatile, but in either case an excess of reagent is always used. The suitable solvents are preferentially those with high polarity. Examples of appropriate solvents include acetonitrile, tetrahydrofuran, dioxane, N,N-dimethylformamide and dimethylsulfoxide. The reaction can be performed between broad temperature margins and the precise temperature chosen is not particularly critical. We have found convenient to carry it out at a temperature between the room temperature and 120° C. The reaction time depends mainly on the nature of the reagent $R_3A$ and the temperature used, but a period between 1 hour and 72 hours will usually suffice. The desired compound can be isolated by concentration of the crude reaction or precipitation with a less polar solvent. The compound obtained in this way is usually pure enough. However, if that is not the case, it can be purified by conventional techniques such as flash chromatography or recrystalization.

Compounds of formula (Ic) or (Id) are salts in which the anion $A^-$ comes from the reagent $R_3A$. If desired, such anion can be changed by using an ionic interchange resin or by selective salt precipitation.

Reflecting the activity of the present compounds, the invention further provides compositions which contain one or more of the compounds of the invention, together with a carrier and optionally other auxilliary agents, if necessary. The compounds of the present invention may be administered on the form of any conventional pharmaceutical formulation, the nature of which will, as is well known, depend on the route of administration and the nature of the condition to be treated. Thus, solid compositions according to the present invention for oral administration include compressed tablets, dispersible powders, granules and capsules. In tablets, one or more of the active component(s) is admixed with at least one inert diluent such as lactose, starch, mannitol, microcrystalline cellulose or calcium phosphate; granulating and desintegrating agents for example corn starch, gelatine, microcrystalline cellulose or polyvinylpyrrolidone; and lubricating agents for example magnesium stearate, stearic acid or talc. The tablets may be coated by known techniques to delay disintegration and absorption in the gastrointestinal tract and, thereby, provide a sustained action over a longer period. Gastric film-coated or enteric film-coated can be made with sugar, gelatin, hydroxypropylcellulose, or acrylic resins. Tablets with a sustained action may also be obtained using an excipient which provides regressive osmosis, such as the galacturonic acid polymers. Formulations for oral use may also be presented as hard capsules of absorbable material, such as gelatin, wherein the active ingredient is mixed with an inert solid diluent and lubricating agents, or pasty materials, such as etoxylated saturated glycerides. Soft gelatin capsules are possible wherein the active ingredient is mixed with water or an oil medium, for example peanut oil, liquid paraffin or olive oil.

Dispersible powders and granules suitable for preparation of a suspension by the addition of water provide the active ingredient in admixture with a dispersing or wetting agent, a suspending agent, such as sodium carboxymethylcellulose, sodium alginate, polyvinylpirrolidone, gum tragacanth, xantham gum, gum acacia, and one or more preservatives, such as methyl or n-propyl p-hydroxybenzoate. Additional excipients, for example sweetening, flavoring and coloring agents may also be present.

Liquid compositions for oral administration include emulsions, solutions, suspensions, syrups and elixirs containing commonly used inert diluents, such as distilled water, ethanol, sorbitol, glycerol, or propylene glycol. Such compositions may also comprise adjuvants such as wetting agents, suspending agents, sweetening, flavoring, perfuming, preserving agents and buffers.

Other compositions for oral administration include spray compositions, which may be prepared by known methods and which comprise one or more active compound(s). The spray compositions will contain a suitable propellent.

Preparations for injection according to the present invention for parenteral administration include sterile aqueous or non-aqueous solutions, suspensions or emulsions, in a non-toxic parentally-acceptable diluent or solvent. Examples of aqueous solvents or suspending media are distilled water for injection, the Ringer's solution, and isotonic sodium chloride solution. Examples of non-aqueous solvents or suspending media are propylene glycol, polyethylene glycol, vegetable oils such as olive oil, or alcohols such as ethanol. These compositions may also include adjuvants such as wetting, preserving, emulsifying and dispersing agents. They may be sterilized by one of the known methods or manufactured in the form of sterile solid compositions which can be dissolved in sterile water or some other sterile injectable medium immediately before use. When all of the components are sterile, the injectables will maintain the sterility if they are manufactured in sterile environment.

A compound of the invention may also be administered in the form of suppositories for rectal administration of the drug, or as creams, ointments jellies, solutions or suspensions for topical use and pessaries for vaginal administration.

The dosage and frequency of dose may vary depending upon symptoms, age and body weight of the patient, as well as upon the route of administration, but, in general, the compounds of the invention may be administered orally in a daily dose of from 5 to 2,000 mg for an adult, preferably a dosage of from 25 to 500 mg, which may be administered either as a single dose or as divided doses.

The invention is further illustrated by the following examples, which describe the preparation of various of the compounds of the invention, as well as the preparations of various of the starting materials which may be used in the Examples for the preparation of the compounds of the present invention.

PREPARATION 1

2-(2-Octadecyloxyethoxy)ethanol

To a cooled suspension (0° C.) of sodium hydride (1.57 g, 36 mmol, 55% in oil) in dry N,N-dimethylformamide (30 mL), was added diethylene glycol (3.82 g, 36 mmol), causing the corresponding hydrogen evolution. Then, a solution of 1-bromooctadecane (10 g, 30 mmol) in N,N-dimethylformamide (20 mL) was added during 5 minutes. The reaction mixture was stirred 20 minutes at 80° C. and 18 hours at 25° C. Finally, it was poured into a mixture of cool water (150 mL) and ether (75 mL). The organic phase was separated, dried over anhydrous sodium sulfate, filtered and concentrated to afford a white solid (12.8 g). The crude was purified by flash chromatography (ethyl acetate:hexane 1:1) to afford the desired product as a white solid (6.07 g, 56% yield).

mp: 45°–46° C.;

IR (KBr)$\nu_{max}$ (cm$^{-1}$): 3350, 2911, 1487, 1466, 1322, 1143, 1077;

$^1$H NMR (80 MHz, CDCl$_3$)δ ppm (TMS): 3.9–3.6 (m, 8H, OCH$_2$CH$_2$OCH$_2$CH$_2$O), 3.46 (t, J=6.4 Hz, 2H, RCH$_2$O), 1.7–0.7 (m, 35H aprox.).

Analysis calcd. for C$_{22}$H$_{46}$O$_3$: C 73.68%; H 12.92%. Found: C 73.74%; H 13.22%.

PREPARATION 2

2-(2-Hexadecyloxyethoxy)ethanol

Following the procedure described in preparation 1, but using 1-bromohexadecane instead of 1-bromooctadecane, the title compound was obtained as an oil in a similar yield.

IR (film)$\nu_{max}$ (cm$^{-1}$): 3350, 2910, 1489, 1467, 1320, 1143, 1078;

$^1$H NMR (80 MHz, CDCl$_3$)δ ppm (TMS): 3.9–3.6 (m, 8H, OCH$_2$CH$_2$OCH$_2$CH$_2$O), 3.48 (t,J=6.3 Hz, 2H, RCH$_2$O), 1.7–0.7 (m, 31H aprox.).

Analysis calcd. for C$_{20}$H$_{42}$O$_3$: C 72.67%; H 12.81%. Found: C 72.88%; H 13.02%.

PREPARATION 3

Diethylene glycol, monopivaloyl ester

To a cooled solution (0° C.) of diethylene glycol (2.65 g, 25 mmol) and pyridine (4.8 mL, 60 mmol) in dichloromethane (20 mL), pivaloyl chloride (2.46 mL, 20 mmol) was added dropwise. The solution was stirred 10 min. at 0° C. and 18 hours at room temperature. Then, the mixture was washed with 2N HCl (2×50 mL), 1N NaOH (1×50 mL) and brine (1×50 mL). The organic phase was dried over anhydrous sodium sulfate and concentrated to yield an oil (2.90 g, 76% yield) which was used in the next step without further purification.

IR (KBr)$\nu_{max}$ (cm$^{-1}$): 3435, 2967, 2871, 1723, 1531, 1478, 1456, 1395, 1364, 1284, 1163, 1131, 1069, 1042;

$^1$H NMR (80 MHz, CDCl$_3$)δ ppm (TMS): 4.3–4.1 (m, 2H, O=COCH$_2$), 3.8–3.5 (m, 6H, CH$_2$OCH$_2$CH$_2$O), 1.21 (s, 9H, Me$_3$C).

PREPARATION 4

Diethylene glycol, mono n-heptadecylcarbamate

To a solution of n-heptadecylisocyanate (16.2 g, 57.5 mmol) in dry pyridine (46.3 mL, 575 mmol) was added diethylene glycol (6.1 g, 57.5 mmol) at room temperature. The mixture was stirred 4.5 hours at 70°–72° C. Chloroform was added and the mixture was washed first with conc. HCl (55 mL) in cool water (120 mL) and then with 10% sodium bicarbonate (100 mL). The organic phase was dried over anhydrous sodium sulfate and concentrated. The reaction crude (16.4 g) was purified by flash chromatography (ethyl acetate: hexane 1:1) to afford the desired product as a white solid (5.53 g, 25%)

mp: 66°–68° C.;

IR (KBr)$\nu_{max}$ (cm$^{-1}$): 3307, 2914, 2845, 1679, 1555, 1461, 1283, 1135;

$^1$H NMR (80 MHz, CDCl$_3$)δ ppm (TMS): 4.71 (broad s, 1H, NH), 4.4–4.1 (m, 2H, O=COCH$_2$), 3.8–3.6 (m, 6H, CH$_2$OCH$_2$CH$_2$O), 3.16 (q,J=6.1Hz, 2H, CH$_2$N), 1.7–0.7 (m, 33H aprox.).

Analysis calcd. for C$_{22}$H$_{45}$NO$_4$: C 68.61%; H 11.70%; N 3.61%. Found: C 68.06%; H 11.82%; N 3.40%.

PREPARATION 5

Diethylene glycol, mono n-pentadecylcarbamate

Following the procedure described in preparation 4, but using n-pentadecylisocyanate instead of n-heptadecylisocyanate, the title compound was obtained in a similar yield.

mp: 55°–59° C.;

IR (KBr)$\nu_{max}$ (cm$^{-1}$): 3305, 2914, 2845, 1680, 1556, 1462, 1291, 1131, 1045;

$^1$H NMR (80 MHz, CDCl$_3$)δ ppm (TMS): 4.77 (broad s, 1H, NH), 4.4–4.1 (m, 2H, O=COCH$_2$), 3.8–3.6 (m, 6H, CH$_2$OCH$_2$CH$_2$O), 3.15 (q,J=6.2 Hz, 2H, CH$_2$N), 1.7–0.7 (m, 29H aprox.).

Analysis calcd. for C$_{20}$H$_{41}$NO$_4$: C 66.82%; H 11.49%; N 3.89%. Found: C 67.03%; H 11.86%; N 4.30%.

PREPARATION 6

1,5-Pentanediol, mono n-pentadecylcarbamate

Following the procedure described in preparation 4, but using 1,5-pentanediol and n-pentadecylisocyanate instead of diethylene glycol and n-heptadecylisocyanate respectively, the title compound was obtained in a similar yield.

mp: 70°–72° C.;

IR (KBr)$\nu_{max}$ (cm$^{-1}$): 3331, 2916, 2846, 1676, 1527, 1465, 1270, 1253, 1237, 1140, 1130, 1057;

$^1$H NMR (80 MHz, CDCl$_3$)δ ppm (TMS): 4.6 (broad s, 1H, NH), 4.07 (t,J=6.2 Hz, 2H, COOCH$_2$), 3.66 (t,J=6 Hz, 2H, CH$_2$OH), 3.14 (q,J=6 Hz, 2H, RCH$_2$N), 1.7–0.7 (m, 29H aprox.).

PREPARATION 7

1,5-Pentanediol, mono-n-heptadecylcarbamate

Following the procedure described in preparation 4, but using 1,5-pentanediol instead of diethylene glycol, the title compound was obtained in a similar yield.

PREPARATION 8

1,6-Hexanediol, mono n-pentadecylcarbamate

Following the procedure described in preparation 4, but using 1,6-hexanediol and n-pentadecylisocyanate, instead of diethylene glycol and n-heptadecylisocyanate respectively, the title compound was obtained in a similar yield.

PREPARATION 9

Thiodiethylene glycol, mono n-pentadecylcarbamate

Following the procedure described in preparation 4, but using thiodiethylene glycol and n-pentadecylisocyanate, instead of diethylene glycol and n-heptadecylisocyanate, respectively, the title compound of this preparation was obtained in a similar yield.

mp: 81°–83° C.;

IR (KBr)$\nu_{max}$ (cm$^{-1}$): 3304, 2948, 2913, 1678, 1543, 1464, 1378, 1316, 1291, 1274, 1147, 1044;

$^1$H NMR (80 MHz, CDCl$_3$)δ ppm (TMS): 4.7 (broad s, 1H, NH), 4.21 (t,J=6.7 Hz, 2H, COOCH$_2$), 3.74 (t,J=6 Hz, 2H, CH$_2$OH), 3.14 (q,J=6 Hz, 2H, RCH$_2$N), 2.71 (t,J=6 Hz, 4H, CH$_2$SCH$_2$), 2.08 (broad s, 1H, OH), 1.6–0.7 (m, 29H aprox.).

Analysis calcd. for $C_{20}H_{41}NO_3S$: C 63.95%; H 11.00%; N 3.73%. Found: C 63.88%; H 11.31%; N 3.89%.

PREPARATION 10

Diethylene glycol, mono 3-phenylpropylcarbamate

Following the procedure described in preparation 4, but using 3-phenylpropylisocyanate instead of n-heptadecylisocyanate, the title compound was obtained in a similar yield.

PREPARATION 11

Diethylene glycol, mono cyclohexylmethylcarbamate

Following the procedure described in preparation 4, but using cyclohexylmethylisocyanate instead of n-heptadecylisocyanate, the title compound was obtained in a similar yield.

PREPARATION 12

Triethylene glycol, mono n-pentadecylcarbamate

Following the procedure described in preparation 4, but using triethylene glycol and n-pentadecylisocyanate, instead of diethylene glycol and n-heptadecylisocyanate, respectively, the title compound was obtained in a similar yield.

IR (KBr) $\nu_{max}(cm^{-1})$: 3306, 2914, 2845, 1680, 1537, 1463, 1270, 1131, 1064;

$^1$H NMR (80 MHz, $CDCl_3$) δ ppm (TMS): 4.88 (broad s, 1H, NH), 4.3-4.1 (m, 2H, O=$COCH_2$), 3.8-3.6 (m, 10H, $CH_2OCH_2CH_2OCH_2CH_2O$), 3.15 (q, J=5.8 Hz, 2H, $CH_2N$), 1.7-0.7 (m, 29H aprox.).

Analysis calcd. for $C_{22}H_{45}NO_5$: C 65.47%; H 11.24%; N 3.47%. Found: C 65.65%; H 11.59%; N 3.41%.

PREPARATION 13

Triethylene glycol, mono n-heptadecylcarbamate

Following the procedure described in preparation 4, but using triethylene glycol instead of diethylene glycol, the title compound was obtained in a similar yield.

IR (KBr) $\nu_{max}(cm^{-1})$: 3310, 2914, 2845, 1683, 1536, 1460, 1270, 1132, 1066;

$^1$H NMR (80 MHz, $CDCl_3$) δ ppm (TMS): 4.80 (broad s, 1H, NH), 4.3-4.1 (m, 2H, O=$COCH_2$), 3.8-3.6 (m, 10H, $CH_2O(CH_2CH_2O)_2$), 3.13 (q, J=6Hz, 2H, $CH_2N$), 1.7-0.7 (m, 33H aprox.).

Analysis calcd. for $C_{24}H_{49}NO_5$: C 66.78%; H 11.44%; N 3.24%. Found: C 66.80%; H 11.55%; N 3.52%.

PREPARATION 14

Tetraethylene glycol, mono n-pentadecylcarbamate

Following the procedure described in preparation 4, but using tetraethylene glycol and n-pentadecylisocyanate, instead of diethylene glycol and n-heptadecylisocyanate, respectively, the title compound was obtained in a similar yield.

IR (KBr) $\nu_{max}(cm^{-1})$: 3306, 2914, 2845, 1682, 1536, 1468, 1260, 1135, 1065;

$^1$H NMR (80 MHz, $CDCl_3$) δ ppm (TMS): 4.81 (broad s, 1H, NH), 4.3-4.1 (m, 2H, O=$COCH_2$), 3.8-3.6 (m, 14H, $CH_2O(CH_2CH_2O)_3$), 3.15 (q, J=5.8 Hz, 2H, $CH_2N$), 1.7-0.7 (m, 29H aprox.).

Analysis calcd. for $C_{24}H_{49}NO_6$: C 64.39%; H 11.03%; N 3.13%. Found: C 64.31%; H 11.31%; N 3.19%.

PREPARATION 15

Dipropylene glycol, mono n-heptadecylcarbamate

Following the procedure described in preparation 4, but using dipropilene glycol instead of diethylene glycol, the title compound was obtained in a similar yield.

PREPARATION 16

Thiodiethylene glycol, mono n-heptadecylcarbamate

Following the procedure described in preparation 4, but using thiodiethylene glycol instead of diethylene glycol, the title compound was obtained in a similar yield.

mp: 85°-86° C.;

IR (KBr) $\nu_{max}(cm^{-1})$: 3304, 2948, 2912, 1677, 1541, 1464, 1377, 1316, 1293, 1275, 1146, 1046;

$^1$H NMR (80 MHz, $CDCl_3$) δ ppm (TMS): 5.0 (broad s, 1H, NH), 4.21 (t, J=6.7 Hz, 2H, $COOCH_2$), 3.74 (t, J=6 Hz, 2H, $CH_2OH$), 3.14 (q, J=6 Hz, 2H, $RCH_2N$), 2.69 (t, J=6 Hz, 4H, $CH_2SCH_2$), 2.6 (broad s, 1H, OH), 1.6-0.7 (m, 29H aprox.).

Analysis calcd. for $C_{22}H_{45}NO_3S$: C 65.46%; H 11.24%; N 3.47%. Found: C 65.73%; H 11.12%; N 3.21%.

PREPARATION 17

2-(2-Hexadecyloxyethylthio)ethanol

Following the procedure described in preparation 1, but using thiodiethylene glycol and 1-bromohexadecane, instead of diethylene glycol and 1-bromooctadecane, respectively, the title compound was obtained in a similar yield.

mp: 49°-50° C.;

IR (KBr) $\nu_{max}(cm^{-1})$: 3379, 2949, 2913, 1468, 1459, 1424, 1362, 1347, 1106, 1048, 1014, 968, 967;

$^1$H NMR (80 MHz, $CDCl_3$) δ ppm (TMS): 3.75 (t, J=6.5 Hz, 2H, $CH_2O$), 3.60 (t, J=6.5 Hz, 2H, $CH_2O$), 3.45 (t, J=6.5 Hz, 2H, $CH_2O$), 2.77 (t, J=6.2 Hz, 2H, $CH_2S$), 2.74 (t, J=6.2 Hz, 2H, $CH_2S$), 2.52 (broad s, 1H, OH), 1.6-0.7 (m, 31H aprox.).

Analysis calcd. for $C_{20}H_{42}O_2S$: C 69.31%; H 12.21%. Found: C 69.70%; H 12.51%.

PREPARATION 18

2-(2-Octadecyloxyethylthio)ethanol

Following the procedure described in preparation 1, but using thiodiethylene glycol instead of diethylene glycol, the title compound was obtained in a similar yield.

mp: 58°-59° C.;

IR (KBr) $\nu_{max}(cm^{-1})$: 3383, 2949, 2914, 1468, 1459, 1425, 1362, 1347, 1107, 1047, 1014, 990, 978;

$^1$H NMR (80 MHz, $CDCl_3$) δ ppm (TMS): 3.75 (t, J=6.5 Hz, 2H, $CH_2O$), 3.60 (t, J=6.5 Hz, 2H, $CH_2O$), 3.45 (t, J=6.5 Hz, 2H, $CH_2O$), 2.77 (t, J=6.2 Hz, 2H, $CH_2S$), 2.74 (t, J=6.2 Hz, 2H, $CH_2S$), 2.52 (broad s, 1H, OH), 1.6-0.7 (m, 35H aprox.).

Analysis calcd. for $C_{22}H_{46}O_2S$: C 70.53%; H 12.38%. Found: C 69.97%; H 12.94%.

EXAMPLE 1

2-(N-((2-(2-Octadecyloxyethoxy)ethoxy)carbonyl)aminomethyl)pyridine

A flame dried flask was charged with the compound obtained in preparation 1 (2.84 g, 7.92 mmol), dry dichloromethane (25 mL) and dry pyridine (1.27 mL, 15.8 mmol). The solution was cooled at 0° C. and phenyl chlorocarbonate (1.09 mL, 8.71 mmol) was slowly added. The mixture was stirred 1 h at 25° C. Then, dichloromethane was added (40 mL) and the solution was washed with 1N aqueous HCl solution. The solution was dried over anhydrous sodium sulfate, filtered and concentrated to afford the corresponding mixed carbonate (3.91 g). This substance (3.88 g, 8.10 mmol), was dissolved in dry chloroform (15 mL) and, then, 2-picolylamine (1.05 mL, 9.73 mmol) was added. The resulting reddish solution was stirred at reflux for 18 h. Dichloromethane (40 mL) was added and the solution washed first with 1N NaOH solution (3×30 mL), then with brine. The organic layer was dried over anhydrous sodium sulfate, filtered and concentrated to afford the desired product as a brown semi-solid (4.17 g). The reaction crude was purified by flash chromatography (ethyl acetate:hexane 3:1) to yield the title compound as a white solid (3.76 g, 96% two steps, overall yield).

mp: 61°-62° C.;

IR (KBr) $\nu_{max}$(cm$^{-1}$): 3220, 3047, 2917, 2844, 1709, 1593, 1570, 1556, 1460, 1322, 1269, 1125;

$^1$H NMR (80 MHz, CDCl$_3$) δ ppm (TMS): 8.54 (broad d, J=5 Hz, 1H, pyr.), 7.67 (dt, J$_d$=1.7 Hz, J$_t$=7.6 Hz, 1H, pyr.), 7.4–7.1 (m, 2H, pyr.), 5.77 (broad s, 1H, NH), 4.50 (d, J=5.4 Hz, 2H, pyr-CH$_2$N), 4.4–4.2 (m, 2H, O=COCH$_2$), 3.8–3.5 (m, 6H, CH$_2$OCH$_2$CH$_2$O), 3.45 (t, J=6.4 Hz, 2H, RCH$_2$O), 1.7–0.7 (m, 35H aprox.).

Analysis calcd. for C$_{29}$H$_{52}$N$_2$O$_4$: C 70.68%; H 10.64%; N 5.68%. Found: C 70.76%; H 10.85%; N 5.65%.

EXAMPLE 2

2-(N-Acetyl-N-((2-(2-octadecyloxyethoxy)ethoxy)carbonyl)aminomethyl)pyridine

In a dry flask, the compound obtained in example 1 (1.5 g, 3.04 mmol), was dissolved in dry dichloromethane (10 mL). The solution was cooled at 0° C. and acetyl chloride (0.28 mL, 3.96 mmol) was slowly added. The reaction mixture was stirred 1.5 h at 0° C. and 48 h at room temperature. Then, triethylamine was added, the mixture was diluted with dichloromethane and washed with water (2×40 mL). The organic layer was dried over anhydrous sodium sulfate, filtered and concentrated to afford a brown solid (2.12 g). Flash chromatography purification (ethyl acetate:hexane 1:1), afforded the desired compound as a white solid (1.54 g, 95%).

IR (film) $\nu_{max}$(cm$^{-1}$): 2913, 2846, 1737, 1697, 1589, 1567, 1463, 1431, 1370, 1338, 1286, 1206, 1138, 1080, 1042;

$^1$H NMR (80 MHz, CDCl$_3$) δ ppm (TMS): 8.50 (broad d, J=4 Hz, 1H, pyr), 7.62 (dt, J$_d$=1.8 Hz, J$_t$=7.5 Hz, 1H, pyr), 7.3–7.0 (m, 2H, pyr), 5.09 (s, 2H, pyr-CH$_2$), 4.4–4.2 (m, 2H, O=COCH$_2$), 3.8–3.5 (m, 6H, CH$_2$OCH$_2$CH$_2$O), 3.40 (t, J=6.5 Hz, 2H, RCH$_2$O), 2.61 (s, 3H, CH$_3$), 1.7–0.7 (m, 35H aprox.).

Analysis calcd. for C$_{31}$H$_{54}$N$_2$O$_5$: C 69.62%; H 10.18%; N 5.23%. Found: C 69.91%; H 10.32%; N 5.25%.

EXAMPLE 3

2-(N-Acetyl-N-((2-(2-octadecyloxyethoxy)ethoxy)carbonyl)aminomethyl)-1-ethylpyridinium iodide A solution of the compound obtained in example 2 (692 mg, 1.29 mmol) in acetonitrile (1 mL) and ethyl iodide (1 mL) was heated at 70° C. for three days. The solution was concentrated in vacuo, the residue was dissolved in dichloromethane and precipitated with ether. The solid was filtered and dried to yield the desired compound as a yellowish powder (693 mg, 77%).

mp: 46°-54° C.;

IR (KBr) $\nu_{max}$(cm$^{-1}$): 3444 (H$_2$O), 2913, 2846, 1745, 1680, 1625, 1579, 1509, 1463, 1370, 1212, 1164, 1119, 1090, 1041;

$^1$H NMR (80 MHz, CDCl$_3$) δ ppm (TMS): 9.67 (broad d, J=6 Hz, 1H, pyr), 8.47 (dt, J$_d$=1.8 Hz, J$_t$=7.8 Hz, 1H, pyr), 8.04 (broad t, J=7 Hz, 1H, pyr), 7.80 (broad d, J=7.8 Hz, 1H, pyr), 5.43 (s, 2H, pyr-CH$_2$), 5.06 (q, J=7.3 Hz, 2H, NEt), 4.6–4.4 (m, 2H, O=COCH$_2$), 3.9–3.5 (m, 6H, CH$_2$OCH$_2$CH$_2$O), 3.43 (t, J=6.5 Hz, 2H, RCH$_2$O), 2.66 (s, 3H, CH$_3$), 1.74 (t, J=7.3 Hz, 3H, NEt), 1.6–0.7 (m, 35H aprox.).

Analysis calcd. for C$_{33}$H$_{59}$IN$_2$O$_5$.H$_2$O: C 55.91%; H 8.67%; N 3.95%. Found: C 55.90%; H 8.76%; N 4.01%.

EXAMPLE 4

2-(N-((2-(2-Hexadecyloxyethoxy)ethoxy)carbonyl)aminomethyl)pyridine

Following the procedure described in example 1, but using the product of preparation 2 instead of the product of preparation 1, the title compound was obtained in a similar yield.

mp: 57°-59° C.;

IR (KBr) $\nu_{max}$(cm$^{-1}$): 3322, 3048, 2917, 2844, 1703, 1598, 1570, 1556, 1461, 1323, 1272, 1128;

$^1$H NMR (80 MHz, CDCl$_3$) δ ppm (TMS): 8.56 (broad d, J=5 Hz, 1H, pyr), 7.70 (dt, J$_d$=1.8 Hz, J$_t$=7.8 Hz, 1H, pyr), 7.4–7.1 (m, 2H, pyr), 5.8 (broad s, 1H, NH), 4.52 (d, J=5.4 Hz, 2H, pyr-CH$_2$), 4.4–4.2 (m, 2H, O=COCH$_2$), 3.8–3.5 (m, 6H, CH$_2$OCH$_2$CH$_2$O), 3.47 (t, J=6.4 Hz, 2H, RCH$_2$O), 1.7–0.7 (m, 31H aprox.).

Analysis calcd. for C$_{27}$H$_{48}$N$_2$O$_4$: C 69.78%; H 10.41%; N 6.03%. Found: C 70.03%; H 10.53%; N 6.33%.

EXAMPLE 5

2-(N-Acetyl-N-((2-(2-hexadecyloxyethoxy)ethoxy)carbonyl)aminomethyl)pyridine

Following the procedure described in example 2, but using the product prepared in example 4, instead of the one prepared in example 1, the title compound was obtained in a similar yield.

IR (film) $\nu_{max}$(cm$^{-1}$): 2913, 2846, 1737, 1699, 1589, 1568, 1566, 1465, 1431, 1370, 1339, 1288, 1205, 1139, 1080, 1042;

$^1$H NMR (80 MHz, CDCl$_3$) δ ppm (TMS): 8.52 (broad d, J=4 Hz, 1H, pyr), 7.63 (dt, J$_d$=1.7 Hz, J$_t$=7.7 Hz, 1H, pyr), 7.3–7.0 (m, 2H, pyr), 5.10 (s, 2H, pyr-CH$_2$), 4.4–4.2 (m, 2H, O=COCH$_2$), 3.8–3.5 (m, 6H, CH$_2$OCH$_2$CH$_2$O), 3.42 (t, J=6.5 Hz, 2H, RCH$_2$O), 2.63 (s, 3H, CH$_3$), 1.7–0.7 (m, 35H aprox.).

Analysis calcd. for C$_{29}$H$_{50}$N$_2$O$_5$: C 68.74%; H 9.94%; N 5.52%. Found: C 68.79%; H 10.05%; N 5.61%.

EXAMPLE 6

2-(N-Acetyl-N-((2-(2-hexadecyloxyethoxy)ethoxy)carbonyl)aminomethyl)-1-ethylpyridinium iodide Following the procedure described in example 3, but using the product prepared in example 5, instead of the one prepared in example 2, the title compound was obtained in a similar yield.

mp: 45°-50° C.;

IR (KBr) $v_{max}$(cm$^{-1}$): 3440 (H$_2$O), 2913, 2845, 1744, 1681, 1625, 1578, 1510, 1466, 1371, 1213, 1165, 1120, 1093, 1044;

$^1$H NMR (80 MHz, CDCl$_3$) δ ppm (TMS): 9.65 (broad d, J=6 Hz, 1H, pyr), 8.44 (dt, J$_d$=1.8 Hz, J$_t$=7.7 Hz, 1H, pyr), 8.03 (broad t, J=7 Hz, 1H, pyr), 7.8 (broad d, J=8.0 Hz, 1H, pyr), 5.41 (s, 2H, pyr-CH$_2$), 5.03 (q, J=7.5 Hz, 2H, NEt), 4.6–4.4 (m, 2H, O=COCH$_2$), 3.9–3.5 (m, 6H, CH$_2$OCH$_2$CH$_2$O), 3.42 (t, J=6.5 Hz, 2H, RCH$_2$O), 2.63 (s, 3H, CH$_3$), 1.72 (t, J=7.5 Hz, 3H, NEt), 1.6–0.7 (m, 31H aprox.).

Analysis calcd. for C$_{31}$H$_{55}$IN$_2$O$_5$.H$_2$O: C 54.69%; H 8.29%; N 4.11%. Found: C 54.67%; H 8.20%; N 4.13%.

EXAMPLE 7

2-(N-((2-(2-Pivaloyloxyethoxy)ethoxy)carbonyl)aminomethyl)pyridine

Following the procedure described in example 1, but using the product prepared in preparation 3, instead of the one prepared in preparation 1, the title compound was obtained as a colorless oil in a similar yield.

IR (film) $v_{max}$(cm$^{-1}$): 3349, 2965, 2869, 1720, 1590, 1566, 1525, 1476, 1455, 1434, 1395, 1362, 1283, 1161, 1044, 994, 942;

$^1$H NMR (80 MHz, CDCl$_3$) δ ppm (TMS): 8.52 (broad d, J=5 Hz, 1H, pyr), 7.66 (dt, J$_d$=1.8 Hz, J$_t$=7.7 Hz, 1H, pyr), 7.4–7.1 (m, 2H, pyr), 5.9 (broad s, 1H, NH), 4.48 (d, J=5.5 Hz, 2H, pyr-CH$_2$), 4.3–4.1 (m, 4H, tert-BuCOOCH$_2$, NCOOCH$_2$), 3.8–3.6 (m, 4H, CH$_2$OCH$_2$)), 1.20 (s, 9H, Me$_3$C).

Analysis calcd. for C$_{16}$H$_{24}$N$_2$O$_5$: C 59.24%; H 7.46%; N 8.64%. Found: C 59.52%; H 7.38%; N 8.77%.

EXAMPLE 8

2-(N-Acetyl-N-((2-(2-pivaloyloxyethoxy)ethoxy)carbonyl)aminomethyl)pyridine

Following the procedure described in example 2, but using the product prepared in example 7, instead of the one prepared in example 1, the title compound was obtained as a colorless oil in a similar yield.

IR (film) $v_{max}$(cm$^{-1}$): 2965, 2870, 1725, 1590, 1567, 1476, 1432, 1369, 1340, 1284, 1207, 1162, 1134, 1097, 1081, 1045;

$^1$H NMR (80 MHz, CDCl$_3$) δ ppm (TMS): 8.49 (broad d, J=5 Hz, 1H, pyr), 7.62 (dt, J$_d$=1.7 Hz, J$_t$=7.7 Hz, 1H, pyr), 7.2–7.7 (m, 2H, pyr), 5.09 (s, 2H, pyr-CH$_2$), 4.4–4.2 (m, 4H, tert-BuCOOCH$_2$, NCOOCH$_2$), 3.7–3.5 (m, 4H, CH$_2$OCH$_2$), 2.61 (s, 3H, CH$_3$), 1.19 (s, 9H, Me$_3$C).

Analysis calcd. for C$_{18}$H$_{26}$N$_2$O$_6$: C 59.00%; H 7.15%; N 7.64%. Found: C 59.23%; H 7.19%; N 7.88%.

EXAMPLE 9

2-(N-Acetyl-N-((2-(2-pivaloyloxyethoxy)ethoxy)carbonyl)aminomethyl)-1-ethylpyridinium iodide Following the procedure described in example 3, but using the product prepared in example 8, instead of the one prepared in example 2, the title compound was obtained as a viscous yellow oil, in a similar yield.

IR (film) $v_{max}$ (cm$^{-1}$): 3440 (H$_2$O), 2969, 2871, 1746, 1714, 1625, 1579, 1509, 1478, 1367, 1285, 1213, 1165, 1132, 1087, 1042, 986;

$^1$H NMR (80 MHz, CDCl$_3$) δ ppm (TMS): 9.60 (broad d, J=5 Hz, 1H, pyr), 8.52 (dt, J$_d$=1.8 Hz, J$_t$=7.5 Hz, 1H, pyr), 8.07 (broad t, J=7 Hz, 1H, pyr), 7.81 (broad d, J=8.0 Hz, 1H, pyr), 5.45 (s, 2H, pyr-CH$_2$), 5.06 (q, J=7.4 Hz, 2H, NEt), 4.6–4.4 (m, 2H, NCOOCH$_2$), 4.3–4.1 (m, 2H, tert-BuCOOCH$_2$), 3.9–3.6 (m, 4H, CH$_2$OCH$_2$), 2.66 (s, 3H, CH$_3$), 1.74 (t, J=7.4 Hz, 3H, NEt), 1.19 (s, 9H, Me$_3$C).

Analysis calcd. for C$_{20}$H$_{31}$IN$_2$O$_6$.3/2H$_2$O: C 43.72%; H 6.23%; N 5.09%. Found: C 43.88%; H 6.01; N 5.08%.

EXAMPLE 10

2-(N-((2-(2-(Heptadecylcarbamoyloxy)ethoxy)ethoxy)carbony)aminomethyl)pyridine

Following the procedure described in example 1, but using the product prepared in preparation 4, instead of the one prepared in preparation 1, the title compound was obtained in a similar yield.

mp: 91°–92° C.;

IR (KBr) $v_{max}$ (cm$^{-1}$): 3301, 3058, 2946, 2913, 2844, 1681, 1542, 1462, 1429, 1280, 1151, 1131, 1110, 1081, 1046;

$^1$H NMR (80 MHz, CDCl$_3$) δ ppm (TMS): 8.53 (broad d, J=5 Hz, 1H, pyr), 7.66 (dt, J$_d$=1.8 Hz, J$_t$=7.5 Hz, 1H, pyr), 7.4–7.1 (m, 2H, pyr), 5.86 (broad s, 1H, NH), 4.77 (broad s, 1H, NH), 4.50 (d, J=5.5 Hz, 2H, pyr-CH$_2$), 4.4–4.1 (m, 4H, COOCH$_2$, COOCH$_2$), 3.86–3.6 (m, 4H, CH$_2$OCH$_2$), 3.15 (q J=6 Hz, 2H, RCH$_2$N), 1.7–0.7 (m, 33H aprox.).

Analysis calcd. for C$_{29}$H$_{51}$N$_3$O$_5$: C 66.76%; H 9.85%; N 8.05%. Found: C 66.79%; H 9.85%; N 8.01%.

EXAMPLE 11

2-(N-Acetyl-N-((2-(2-(heptadecylcarbamoyloxy)ethoxy)ethoxy)carbonyl)aminomethyl)pyridine Following the procedure described in example 2, but using the product prepared in example 10, instead of the one prepared in example 1, the title compound was obtained in a similar yield.

mp: 60°–61° C.;

IR (KBr) $v_{max}$ (cm$^{-1}$): 3342, 2912, 2845, 1743, 1697, 1681, 1589, 1524, 1466, 1433, 1417, 1372, 1338, 1199, 1077;

$^1$H NMR (80 MHz, CDCl$_3$) δ ppm (TMS): 8.50 (broad d, J=5 Hz, 1H, pyr), 7.60 (dt, J$_d$=1.8 Hz, J$_t$=7.5 Hz, 1H, pyr), 7.2–7.0 (m, 2H, pyr), 5.10 (s, 2H, pyr-CH$_2$), 4.4–4.2 (m, 2H, COOCH$_2$), 4.2–4.0 (m, 2H, COOCH$_2$), 3.7–3.4 (m, 4H, CH$_2$OCH$_2$), 3.14 (q, J=6 Hz, 2H, RCH$_2$N), 2.62 (s, 3H, CH$_3$), 1.7–0.7 (m, 33H, aprox.).

Analysis calcd. for C$_{31}$H$_{53}$N$_3$O$_6$: C 66.04%; H 9.48%; N 7.45%. Found: C 65.88%; H 9.67%; N 7.17%.

EXAMPLE 12

2-(N-Acetyl-N-((2-(2-heptadecylcarbamoyloxy)ethoxy)ethoxy)carbonyl)aminomethyl)-1-ethylpyridium chloride a)
2-(N-Acetyl-N-((2-(2-heptadecylcarbamoyloxy)ethoxy)ethoxy)carbonyl)aminomethyl)-1-ethylpyridium iodide Following the procedure described in example 3, but using the product prepared in example 11, instead of the one prepared in example 2, the iodide was obtained in a similar yield.

mp: 44°–46° C.;

IR (KBr) $v_{max}$(cm$^{-1}$): 3441 (H$_2$O), 2913, 2846, 1687, 1625, 1579, 1524, 1463, 1370, 1338, 1211;

$^1$H NMR (80 MHz, CDCl$_3$) δ ppm (TMS): 9.61 (broad d, J=6 Hz, 1H, pyr), 8.46 (broad t, J=7.5 Hz, 1H, pyr), 8.04 (broad t, J=7 Hz, 1H, pyr), 7.80 (broad d, J=7.5 Hz, 1H, pyr), 5.46 (s, 2H, pyr-CH$_2$), 5.08 (q, J=7 Hz, 2H, NEt), 4.6–4.4 (m, 2H, COOCH$_2$), 4.3–4.1 (m, 2H, COOCH$_2$), 3.9–3.6 (m, 4H, CH$_2$OCH$_2$), 3.13 (q, J=6 Hz, 2H, RCH$_2$N), 2.66 (s, 3H, CH$_3$), 1.74 (t, J=7 Hz, 3H, NEt), 1.7–0.7 (m, 33H approx.).

Analysis calcd. for C$_{33}$H$_{58}$IN$_3$O$_6$.3/2H$_2$O: C 53.08%; H 8.23%; N 5.62%. Found: C 53.07%; H 7.94%; N 5.52%.

b) Obtention of the Title Compound

A solution of the compound obtained in part (a) (748 mg, 1.10 mmol) in 70% aqueous methanol was eluted through an ionic interchange column IRA-410 (chloride form). The filtrate was concentrated to dryness and recrystallized in ether: acetone to give the desired compound as a white powder (638 mg, 92%)

mp: 46°–47° C.;

IR (KBr) $\nu_{max}$ (cm$^{-1}$): 3295, 3051, 2914, 2845, 1740, 1686, 1624, 1540, 1460, 1370, 1346, 1222;

Analysis calcd. for C$_{33}$H$_{58}$ClN$_3$O$_6$.½H$_2$O: C 62.19%; H 9.33%; N 6.59%. Found: C 61.96%; H 9.71%; N 6.51%.

EXAMPLE 13

2-(N-((2-(2-(Heptadecylcarbamoyloxy)ethoxy)ethoxy)-carbonyl)aminomethyl)-1-ethylpyridinium iodide Following the procedure described in example 3, but using the product prepared in example 10, instead of the one prepared in example 2, the title compound was obtained in a similar yield.

mp: 53°–68° C.;

IR (KBr) $\nu_{max}$ (cm$^{-1}$): 3321, 2913, 2846, 1702, 1625, 1518, 1463, 1255, 1125, 1043;

$^1$H NMR (80 MHz, CDCl$_3$) δ ppm (TMS): 9.22 (broad d, J=5 Hz, 1H, pyr), 8.6–7.9 (m, 3H, pyr), 7.1 (broad s, 1H, NH), 5.1 (m, 3H, NH, NEt), 4.94 (d, J=7 Hz, 2H, Pyr-CH$_2$), 4.3–4.1 (m, 4H, COOCH$_2$, COOCH$_2$), 3.8–3.6 (m, 4H, CH$_2$OCH$_2$), 3.14 (q, J=6 Hz, 2H, RCH$_2$N), 1.7 (t, J=7 Hz, 3H, NEt), 1.7–0.7 (m, 33H aprox.).

Analysis calcd. for C$_{31}$H$_{56}$IN$_3$O$_5$: C 54.94%; H 8.33%; N 6.20%. Found: C 54.80%; H 8.44%; N 6.07%.

EXAMPLE 14

2-(N-Acetyl-N-((2-(2-(heptadecylcarbamoyloxy)ethoxy)ethoxy)carbonyl)aminomethyl)-1-methylpyridinium iodide Following the procedure described in example 3, but using the product prepared in example 11 and methyl iodide, instead of the one prepared in example 2 and ethyl iodide, respectively, the title compound was obtained in a similar yield.

mp: 48°–70° C.;

IR (KBr) $\nu_{max}$ (cm$^{-1}$): 3325 (H$_2$O), 2913, 2846, 1750, 1693, 1626, 1580, 1513, 1463, 1428, 1368, 1332, 1212, 1128, 1084, 1042;

$^1$H NMR (80 MHz, CDCl$_3$) δ ppm (TMS): 9.41 (broad d, J=5 Hz, 1H, pyr), 8.46 (broad t, J=7.5 Hz, 1H, pyr), 5.43 (s, 2H, Pyr-CH$_2$), 5.1 (broad s, 1H, NH), 4.69 (s, 3H, NCH$_3$), 4.6–4.4 (m, 2H, COOCH$_2$), 4.3–4.1 (m, 2H, COOCH$_2$), 3.9–3.6 (m, 4H, CH$_2$OCH$_2$), 3.12 (q, J=6 Hz, 2H, RCH$_2$N), 2.63 (s, 3H, CH$_3$), 1.7–0.7 (m, 33H aprox.).

Analysis calcd. for C$_{32}$H$_{56}$IN$_3$O$_6$.3/2H$_2$O: C 52.45%; H 8.11%; N 5.73%. Found: C 52.48%; H 7.98%; N 5.59%.

EXAMPLE 15

2-(N-Ethoxycarbonyl-N-((2-(2-(heptadecylcarbamoyloxy)ethoxy)ethoxy)carbonyl)aminomethyl)-pyridine Following the procedure described in example 2, but using the product prepared in example 10 and ethyl chlorocarbonate, instead of the one prepared in example 1 and acetyl chloride, respectively, the title compound was obtained in a similar yield.

mp: 57°–59° C.;

IR (KBr) $\nu_{max}$ (cm$^{-1}$): 3347, 2912, 2845, 1788, 1754, 1711, 1681, 1591, 1566, 1525, 1468, 1433, 1393, 1371, 1338, 1302, 1274, 1260, 1246, 1204, 1099, 1043, 1022;

$^1$H NMR (80 MHz, CDCl$_3$) δ ppm (TMS): 8.52 (broad d, J=5 Hz, 1H, pyr), 7.64 (dt, J$_d$=1.8 Hz, J$_t$=7.5 Hz, 1H, pyr), 7.3–7.1 (m, 2H, pyr), 5.0 (broad s, 1H, NH), 5.04 (s, 2H, Pyr-CH$_2$), 4.5–4.1 (m, 4H, COOCH$_2$, COOCH$_2$), 4.26 (q, J=7.1 Hz, 2H, OEt), 3.8–3.5 (m, 4H, CH$_2$OCH$_2$), 3.14 (q, J=6 Hz, 2H, RCH$_2$N), 1.7–0.7 (m, 36H approx.).

Analysis calcd. for C$_{32}$H$_{55}$N$_3$O$_7$: C 64.73%; H 9.33%; N 7.08%. Found: C 64.78%; H 9.20%; N 6.83%.

EXAMPLE 16

2-(N-Ethoxycarbonyl-N-((2-(2-(heptadecylcarbamoyloxy)ethoxy)ethoxy)carbonyl)aminomethyl)-1-ethylpyridinium iodide Following the procedure described in example 3, but using the product prepared in example 15, instead of the one prepared in example 2, the title compound was obtained in a similar yield.

mp: 45°–50° C.;

IR (KBr) $\nu_{max}$ (cm$^{-1}$): 3445, 2914, 2846, 1788, 1758, 1692, 1625, 1580, 1524, 1463, 1372, 1388, 1297, 1215, 1104, 1018;

$^1$H NMR (80 MHz, CDCl$_3$) δ ppm (TMS): 9.76 (broad d, J=6 Hz, 1H, pyr), 8.53 (dt, J$_d$=1.8 Hz, J$_t$=6.7 Hz, 1H, pyr), 8.09 (broad t, J=6.7 Hz, 1H, pyr), 7.84 (broad d, J=8 Hz, 1H, pyr), 5.45 (s, 2H, Pyr-CH$_2$), 5.09 (q, J=7.3 Hz, 2H, NEt), 5.0 (broad s, 1H, NH), 4.34 (q, J=7.0 Hz, 2H, OEt), 4.5–4.3 (m, 2H, COOCH$_2$), 4.3–4.1 (m, 2H, COOCH$_2$), 3.9–3.6 (m, 4H, CH$_2$OCH$_2$), 3.13 (q, J=5.8 Hz, 2H, RCH$_2$N), 1.73 (t, J=7.3 Hz, 3H, NEt), 1.34 (t, J=7.0 Hz, 3H, OEt), 1.6–0.7 (m, 33H, aprox.).

Analysis calcd. for C$_{34}$H$_{60}$IN$_3$O$_7$.½H$_2$O: C 53.50%; H 8.12%; N 5.50%. Found: C 53.65%; H 8.27%; N 5.44%.

EXAMPLE 17

2-(N-((2-(2-(Pentadecylcarbamoyloxy)ethoxy)ethoxy)-carbonyl)aminomethyl)pyridine Following the procedure described in example 1, but using the product obtained in preparation 5, instead of the one obtained in preparation 1, the title compound was obtained in a similar yield.

mp: 86°–87° C.;

IR (KBr) $\nu_{max}$ (cm$^{-1}$): 3303, 3045, 2949, 2913, 2846, 1680, 1584, 1539, 1462, 1260, 1155, 1125, 1111, 1082, 1050;

$^1$H NMR (80 MHz, CDCl$_3$) δ ppm (TMS): 8.53 (broad d, J=5 Hz, 1H, pyr), 7.67 (dt, J$_d$=1.5 Hz, J$_t$=7.5 Hz, 1H, pyr), 7.4–7.1 (m, 2H, pyr), 5.8 (broad s, 1H, NH), 4.8 (broad s, 1H, NH), 4.50 (d, J=5.4 Hz, 2H, Pyr-CH$_2$), 4.4–4.1 (m, 4H, COOCH$_2$, COOCH$_2$), 3.8–3.6 (m, 4H, CH$_2$OCH$_2$), 3.14 (q, J=6 Hz, 2H, RCH$_2$N), 1.7–0.7 (m, 29H aprox.).

Analysis calcd. for $C_{27}H_{47}N_3O_5$: C 65.69%; H 9.59%; N 8.51%. Found: C 65.88%; H 9.22%; N 8.61%.

EXAMPLE 18

2-(N-Acetyl-N-((2-(2-(pentadecylcarbamoyloxy)ethoxy)ethoxy)carbonyl)aminomethyl)pyridine Following the procedure described in example 2, but using the product prepared in example 17, instead of the one prepared in example 1, the title compound was obtained in a similar yield.

mp: 53°-55° C.;

IR (KBr) $\nu_{max}$ (cm$^{-1}$): 3338, 2912, 2845, 1742, 1681, 1589, 1525, 1463, 1433, 1417, 1373, 1338, 1253, 1200;

$^1$H NMR (80 MHz, CDCl$_3$) δ ppm (TMS): 8.50 (d, J=4 Hz, 1H, pyr), 7.62 (dt, $J_d$=1.8 Hz, $J_t$=7.1 Hz, 1H, pyr), 7.3-7.0 (m, 2H, pyr), 5.11 (s, 2H, Pyr-CH$_2$), 5.1 (broad s, 1H, NH), 4.4-4.2 (m, 2H, COOCH$_2$), 4.2-4.0 (m, 2H, COOCH$_2$), 3.7-3.4 (m, 4H, CH$_2$OCH$_2$), 3.15 (q, J=6 Hz, 2H, RCH$_2$N), 2.63 (s, 3H, CH$_3$), 1.7-0.7 (m, 29H aprox.).

Analysis calcd. for $C_{29}H_{49}N_3O_6$: C 65.01%; H 9.22%; N 7.84%. Found: C 64.66%; H 9.67%; N 7.59%.

EXAMPLE 19

2-(N-Acetyl-N-((2-(2-(pentadecylcarbamoyloxy)ethoxy)ethoxy)carbonyl)aminomethyl)-1-ethylpyridinium iodide Following the procedure described in example 3, but using the product prepared in example 18, instead of the one prepared in example 2, the title compound was obtained in a similar yield.

mp: 71°-75° C.;

IR (KBr) $\nu_{max}$ (cm$^{-1}$): 3441, 2920, 2849, 1747, 1696, 1625, 1580, 1514, 1446, 1370, 1338, 1213, 1163, 1134, 1086;

$^1$H NMR (80 MHz, CDCl$_3$) δ ppm (TMS): 9.60 (broad d, J=6 Hz, 1H, pyr), 8.51 (t, J=7.5 Hz, pyr), 8.04 (t, J=6.5 Hz, 1H, pyr), 7.82 (d, J=8 Hz, 1H, pyr), 5.46 (s, 2H, Pyr-CH$_2$), 5.06 (q, J=7.3 Hz, 3H, NH, NEt), 4.6-4.4 (m, 2H, COOCH$_2$), 4.3-4.1 (m, 2H, COOCH$_2$), 3.9-3.6 (m, 4H, CH$_2$OCH$_2$), 3.14 (q, J=5.6 Hz, 2H, RCH$_2$N), 2.66 (s, 3H, CH$_3$), 1.74 (t, J=7.3 Hz, 3H, NEt), 1.7-0.7 (m, 29H aprox.).

Analysis calcd. for $C_{31}H_{54}IN_3O_6 \cdot \frac{1}{2}H_2O$: C 53.14%; H 7.91%; N 5.99%. Found: C 52.95%; H 7.93%; N 5.82%.

EXAMPLE 20

2-(N-Acetyl-N-((2-(2-(pentadecylcarbamoyloxy)ethoxy)ethoxy)carbonyl)aminomethyl)-1-propylpyridinium iodide Following the procedure described in example 3, but using the product prepared in example 18 and isopropyl iodide, instead of the one prepared in example 2 and ethyl iodide, the title compound was obtained in a similar yield.

IR (film) $\nu_{max}$ (cm$^{-1}$): 3331, 2919, 2849, 1747, 1693, 1624, 1578, 1513, 1449, 1367, 1338, 1220, 1162, 1131, 1088, 1043, 986;

$^1$H NMR (80 MHz, CDCl$_3$) δ ppm (TMS): 9.58 (d, J=6 Hz, 1H, pyr), 8.54 (dt, $J_d$=1.8 Hz, $J_t$=7.5 Hz, 1H, pyr), 8.05 (broad t, J=6.0 Hz, 1H, pyr), 7.85 (broad d, J=8 Hz, 1H, pyr), 5.44 (s, 2H, Pyr-CH$_2$), 4.95 (t, J=7.3 Hz, 3H, NPr, NH), 4.6-4.4 (m, 2H, COOCH$_2$), 4.3-4.0 (m, 2H, COOCH$_2$), 3.9-3.6 (m, 4H, CH$_2$OCH$_2$), 3.14 (q, J=6.2 Hz, 2H, RCH$_2$N), 2.66 (s, 3H, CH$_3$), 2.10 (m, 2H, Pr), 1.7-0.7 (m, 32H aprox.).

Analysis calcd. for $C_{32}H_{56}IN_3O_6 \cdot \frac{1}{2}H_2O$: C 53.44%; H 8.06%; N 5.84%. Found: C 53.44%; H 8.12%; N 5.90%.

EXAMPLE 21

2-(N-Ethoxycarbonyl-N-((2-(2-(pentadecylcarbamoyloxy)ethoxy)ethoxy)carbonyl)aminomethyl)pyridine Following the procedure described in example 2, but using the product prepared in example 17 and ethyl chlorocarbonate, instead of the one prepared in example 1 and acetyl chloride, the title compound was obtained.

mp: 52°-53° C.;

IR (KBr) $\nu_{max}$ (cm$^{-1}$): 3563, 2918, 2847, 1788, 1681, 1594, 1530, 1463, 1429, 1376, 1350, 1210, 1155, 1092;

$^1$H NMR (80 MHz, CDCl$_3$) δ ppm (TMS): 8.53 (broad d, J=5 Hz, 1H pyr), 7.64 (dt, $J_d$=1.7 Hz, $J_t$=7.5 Hz, 1H, pyr), 7.3-7.0 (m, 2H, pyr), 5.04 (s, 2H, Pyr-CH$_2$), 5.0 (broad s, 1H, NH), 4.5-4.3 (m, 2H, COOCH$_2$), 4.25 (q, J=7.1 Hz, 2H, OEt), 4.3-4.0 (m, 2H, COOCH$_2$), 3.8-3.5 (m, 4H, CH$_2$OCH$_2$), 3.14 (q, J=6.1 Hz, 2H, RCH$_2$N), 1.7-0.7 (m 32H aprox.).

Analysis calcd. for $C_{31}H_{51}N_3O_7$: C 64.44%; H 8.89%; N 7.27%. Found: C 64.27%; H 9.20%; N 7.28%.

EXAMPLE 22

2-(N-Ethoxycarbonyl-N-((2-(2-(pentadecylcarbamoyloxy)ethoxy)ethoxy)carbonyl)aminomethyl)-1-ethylpyridinium iodide Following the procedure described in example 3, but using the product obtained in example 21, instead of the one prepared in example 2, the title compound of this example was obtained.

mp: 30°-42° C.;

IR (KBr) $\nu_{max}$ (cm$^{-1}$): 3345 (H$_2$O), 2921, 2849, 1792, 1760, 1701, 1624, 1518, 1448, 1372, 1338, 1299, 1218, 1104, 1019;

$^1$H NMR (80 MHz, CDCl$_3$) δ ppm (TMS): 9.74 (d, J=5 Hz, 1H, pyr), 8.56 (broad t, J=7.5 Hz, 1H, pyr), 8.12 (broad t, J=6 Hz, 1H, pyr), 7.85 (d, J=8 Hz, 1H, pyr), 5.46 (s, 2H, Pyr-CH$_2$), 5.09 (q, J=7.3 Hz, 3H, NEt, NH), 4.5-4.3 (m, 2H, COOCH$_2$), 4.34 (q, J=7.1 Hz, 2H, OEt), 4.3-4.1 (m, 2H, COOCH$_2$), 3.9-3.6 (m, 4H, CH$_2$OCH$_2$), 3.14 (q, J=6.1 Hz, 2H, RCH$_2$N), 1.74 (t, J=7.3 Hz, 3H, NEt), 1.7-0.7 (m, 32H aprox.).

Analysis calcd. for $C_{32}H_{56}IN_3O_7 \cdot \frac{1}{2}H_2O$: C 52.59%; H 7.86%; N, 5.75%. Found: C 52.62%; H 7.83%; N 5.82%.

EXAMPLE 23

2-(N-Isobutyloxycarbonyl-N-((2-(2-(pentadecylcarbamoyloxy)ethoxy)ethoxy)carbonyl)aminomethyl)pyridine Following the procedure described in example 2, but using the product obtained in example 17 and isobutyl chlorocarbonate, instead of the one prepared in example 1 and acetyl chloride, the title compound was obtained as a colorless oil.

IR (film) $\nu_{max}$ (cm$^{-1}$): 3368, 2919, 2850, 1789, 1752, 1721, 1592, 1524, 1463, 1434, 1393, 1378, 1345, 1291, 1247, 1204, 1107;

$^1$H NMR (80 MHz, CDCl$_3$) δ ppm (TMS): 8.54 (broad d, J=5 Hz, 1H, pyr), 7.64 (dt, $J_d$=1.8 Hz, $J_t$=7.5 Hz, 1H, pyr), 7.3-7.0 (m, 2H, pyr), 5.05 (s, 2H, Pyr-CH$_2$), 5.0 (broad s, 1H, NH), 4.5-4.2 (m, 2H, COOCH$_2$), 4.2-4.0 (m, 2H, COOCH$_2$), 3.97 (d, J=6.4 Hz, 2H, i-Bu), 3.8–3.5 (m, 4H, CH$_2$OCH$_2$), 3.14 (q, J=6 Hz, 2H, RCH$_2$N), 2.1–1.6 (m, 1H, i-Bu), 1.6–0.7 (m, 35H aprox.).

Analysis calcd. for C$_{32}$H$_{55}$N$_3$O$_7$: C 64.72%; H 9.33%; N 7.07%. Found: C 64.45%; H 9.44%; N 6.94%.

EXAMPLE 24

2-(N-Isobutyloxycarbonyl-N-((2-(2-(pentadecylcarbamoyloxy)ethoxy)ethoxy)carbonyl)aminomethyl)-1-ethylpyridinium iodide Following the procedure described in example 3, but using the product prepared in example 23, the title compound was obtained as a paste.

$^1$H NMR (80 MHz, CDCl$_3$) δ ppm (TMS): 9.67 (broad d, J=6 Hz, 1H, pyr), 8.65 (broad t, J=7.8 Hz, 1H, pyr), 8.15 (broad t, J=6.8 Hz, pyr), 7.88 (broad d, J=8 Hz, 1H, pyr), 5.48 (s, 2H, Pyr-CH$_2$), 5.06 (q, J=7.4 Hz, 3H, NEt, NH), 4.5–4.3 (m, 2H, COOCH$_2$), 4.3–4.0 (m, 2H, COOCH$_2$), 4.04 (d, J=6.4 Hz, 2H, i-Bu), 3.8–3.5 (m, 4H, CH$_2$OCH$_2$), 3.13 (q, J=5.8 Hz, 2H, RCH$_2$N), 2.2–1.7 (m, 1H, i-Bu), 1.73 (t, J=7.4 Hz, 3H, NEt), 1.6–0.7 (m,35H aprox.).

EXAMPLE 25

2-(N-Isobutyloxycarbonyl-N-((2-(2-(pentadecylcarbamoyloxy)ethoxy)ethoxy)carbonyl)aminomethyl)-1-ethylpyridinium chloride Following the procedure described in example 12b, but using the product prepared in example 24, instead of the one prepared in example 12a, the title compound was obtained as a yellow oil.

IR (film) $v_{max}$ (cm$^{-1}$): 3382 (H$_2$O), 2953, 2919, 1791, 1758, 1696, 1625, 1524, 1449, 1377, 1295, 1216, 1108;

$^1$H NMR (80 MHz, CDCl$_3$) δ ppm (TMS): 10.10 (d, J=5 Hz, 1H, pyr), 8.47 (t, J=7.3 Hz, 1H, pyr), 8.09 (t, J=7 Hz, 1H, pyr), 7.78 (broad d, J=8 Hz, 1H, pyr), 5.43 (s, 2H, Pyr-CH$_2$), 5.17 (q, J=7.2 Hz, 3H, NEt, NH), 4.5–4.3 (m, 2H, COOCH$_2$), 4.2–4.0 (m, 2H, COOCH$_2$), 4.06 (d, J=6.5 Hz, 2H, i-Bu), 3.8–3.6 (m, 4H, CH$_2$OCH$_2$), 3.12 (q, J=6 Hz, 2H, RCH$_2$N), 2.3–1.7 (m, 1H, i-Bu) 1.72 (t, J=7.2 Hz, 3H, NEt), 1.7–0.7 (m, 35H aprox.).

Analysis calcd. for C$_{34}$H$_{60}$N$_3$ClO$_7$.H$_2$O: C 60.38%; H 9.24%; N 6.21%. Found: C 60.56%; H 9.36%; N 6.15%.

EXAMPLE 26

2-(N-((5-(Heptadecylcarbamoyloxy)pentoxy)carbonyl)aminomethyl)pyridine

Following the procedure described in example 1, but using the product obtained in preparation 7, instead of the one obtained in preparation 1, the title compound was obtained in a similar yield.

EXAMPLE 27

2-(N-Acetyl-N-((5-(heptadecylcarbamoyloxy)pentoxy)carbonyl)aminomethyl) pyridine Following the procedure described in example 2, but using the product obtained in example 26, instead of the one obtained in preparation 1, the title compound was obtained in a similar yield.

EXAMPLE 28

2-(N-Acetyl-N-((5-(heptadecylcarbamoyloxy)pentoxy)carbonyl)aminomethyl)-1-ethylpyridinium iodide Following the procedure described in example 3, but using the product obtained in example 27, instead of the one obtained in preparation 1, the title compound was obtained in a similar yield.

EXAMPLE 29

2-(N-((5-(Pentadecylcarbamoyloxy)pentoxy)carbonyl)aminomethyl) pyridine

Following the procedure described in example 1, but using the product obtained in example 6, instead of the one obtained in preparation 1, the title compound was obtained in a similar yield.

IR (film)$v_{max}$ (cm$^{-1}$): 3307, 2915, 2845, 1672, 1589, 1530, 1464, 1439, 1260, 1143, 1068, 1055, 983;

$^1$H NMR (80 MHz, CDCl$_3$) δ ppm (TMS): 8.53 (broad d, J=5.6Hz, 1H, pyr), 7.66 (dt, J$_d$=1.8 Hz, J$_t$=7.6 Hz, ,1H, pyr), 7.3–7.0 (m, 2H, pyr), 5.7 (broad s, 1H, NH), 4.7 (broad s, 1H, NH), 4.48 (d, J=5.4 Hz, 2H, Pyr-CH$_2$), 4.2–3.9 (m, 4H, COOCH$_2$, COOCH$_2$), 3.14 (q, J=6.1 Hz,2H, RCH$_2$N), 1.7–0.7 (m, 29H aprox.).

EXAMPLE 30

2-(N-Acetyl-N-((5-(pentadecylcarbamoyloxy)pentoxy)carbonyl)aminomethyl) pyridine Following the procedure described in example 2, but using the product obtained in example 29, instead of the one obtained in example 1, the title compound was obtained.

IR (film) $v_{max}$ (cm$^{-1}$): 3335, 2912, 2844, 1736, 1680, 1590, 1567, 1530, 1463, 1433, 1338, 1204, 1154, 1077, 1046;

$^1$H NMR (80 MHz, CDCl$_3$) δ ppm (TMS): 8.51 (dq, J$_q$=1.3 Hz, J$_d$=5 Hz, 1H, pyr), 7.63 (dt, J$_d$=7.5 Hz, J$_t$=1.8 Hz, 1H, pyr), 7.3–7.0 (m, 2H, pyr), 5.08 (s, 2H, Pyr-CH$_2$), 4.8 (broad s, 1H, NH), 4.2–3.9 (m, 4H, COOCH$_2$, COOCH$_2$), 3.13 (q, J=6 Hz, 2H, RCH$_2$N), 2.63 (s, 3H, CH$_3$), 0.7–0.7 (m, 29H aprox.).

EXAMPLE 31

2-(N-Acetyl-N-((5-(pentadecylcarbamoyloxy)pentoxy)carbonyl)aminomethyl)-1-ethylpyridinium iodide Following the procedure described in example 3, but using the product obtained in example 30, instead of the one obtained in example 2, the title compound was obtained.

mp: 31°–33° C.;

IR (KBr) $v_{max}$ (cm$^{-1}$): 3335, 3030, 2918, 2847, 1735, 1705, 1677, 1625, 1578, 1524, 1463, 1446, 1367, 1344, 1222, 1164, 1084;

$^1$H NMR (80 MHz, CDCl$_3$) δ ppm (TMS): 9.64 (broad d, J=5.6 Hz, 1H, pyr), 8.45 (broad t, J=7.5 Hz, 1H, pyr), 8.04 (broad t, J=7 Hz, 1H, pyr), 7.42 (broad d, J=8 Hz, 1H, pyr), 5.42 (s, 2H, Pyr-CH$_2$), 5.08 (q, J=7.3 Hz, 2H, NEt), 5.0 (broad s, 1H, NH), 4.32 (t, J=6.2 Hz, 2H, COOCH$_2$), 4.01 (t, J=6.3 Hz, 2H, COOCH$_2$), 3.13 (q, J=6 Hz, 2H, RCH$_2$N), 2.64 (s, 3H, CH$_3$), 1.7–0.7 (m, 32H aprox.).

Analysis calcd. for C$_{32}$H$_{56}$IN$_3$O$_5$.½H$_2$O: C 55.24%; H 8.33%; N 6.04%. Found: C 55.22%; H 8.51%; N 6.19%.

EXAMPLE 32

2-(N-((6-(Pentadecylcarbamoyloxy)hexyloxy)carbonyl)aminomethyl) pyridine

Following the procedure described in example 1, but using the product obtained in preparation 8, instead of the one obtained in preparation 1, the title compound was obtained in a similar yield.

EXAMPLE 33

2-(N-Acetyl-N-((6-(pentadecylcarbamoyloxy)hexyloxy)carbonyl)aminomethyl) pyridine Following the procedure described in example 2, but using the product obtained in example 32, instead of the one obtained in example 1, the title compound was obtained in a similar yield.

EXAMPLE 34

2-(N-Acetyl-N-((6-(pentadecylcarbamoyloxy)hexyloxy)carbonyl)aminomethyl)-1-ethylpyridinium iodide Following the procedure described in example 3, but using the product obtained in example 33, instead of the one obtained in example 2, the title compound was obtained in a similar yield.

EXAMPLE 35

2-(N-((2-(2-(pentadecylcarbamoyloxy)ethylthio)ethoxy)carbonyl) aminomethyl) pyridine Following the procedure described in example 1, but using the product obtained in preparation 9, instead of the one obtained in preparation 1, the title compound was obtained in a similar yield.

IR (KBr) $\nu_{max}$ (cm$^{-1}$): 3306, 3057, 2913, 2844, 1680, 1624, 1589, 1540, 1464, 1433, 1377, 1289, 1272, 1147, 1073, 1046;

$^1$H NMR (80 MHz, CDCl$_3$) δ ppm (TMS): 8.53 (broad d, J=5 Hz, 1H, pyr), 7.65 (broad t, J=7.5 Hz, 1H, pyr), 7.3–7.0 (m, 2H, pyr), 5.8 (broad s, 1H, NH), 5.0 (broad s, 1H, NH), 4.49 (d, J=5.5 Hz, 2H, Pyr-CH$_2$), 4.3–4.1 (m, 4H, COOCH$_2$, COOCH$_2$), 3.13 (q, J=6.0 Hz, 2H, RCH$_2$N), 2.79 (t, J=6.5 Hz, 4H, CH$_2$SCH$_2$), 1.7–0.7 (m, 29H aprox.).

EXAMPLE 36

2-(N-Acetyl-N-((2-(2-(pentadecylcarbamoyloxy)ethylthio)ethoxy)carbonyl) aminomethyl) pyridine Following the procedure described in example 2, but using the product obtained in example 35, instead of the one obtained in example 1, the title compound was obtained in a similar yield.

IR (KBr) $\nu_{max}$ (cm$^{-1}$): 3324, 2915, 2846, 1740, 1681, 1590, 1530, 1464, 1424, 1384, 1372, 1350, 1269, 1254, 1204, 1142, 1078;

$^1$H NMR (80 MHz, CDCl$_3$) δ ppm (TMS): 8.50 (broad d, J=4 Hz, 1H, pyr), 7.63 (dt, J$_t$=1.8 Hz, J$_d$=7.4 Hz, 1H, pyr), 7.3–7.0 (m, 2H, pyr), 5.08 (s, 2H, Pyr-CH$_2$), 4.9 (broad s, 1H, NH), 4.30 (t, J=7 Hz, 2H, COOCH$_2$), 4.16 (t, J=4.7 Hz, 2H, COOCH$_2$), 3.14 (q, J=6 Hz, 2H, RCH$_2$N), 2.69 (t, J=6.7 Hz, 4H, CH$_2$SCH$_2$), 2.62 (s, 3H, CH$_3$), 1.7–0.7 (m, 29H aprox.).

EXAMPLE 37

2-(N-Acetyl-N-((2-(2-(pentadecylcarbamoyloxy)ethylthio)ethoxy)carbonyl) aminomethyl)-1-ethylpyridinium iodide Following the procedure described in example 3, but using the product obtained in example 36, instead of the one obtained in example 2, the title compound was obtained in a similar yield.

mp: 46°–48° C.;

IR (KBr) $\nu_{max}$ (cm$^{-1}$): 3396, 2915, 2846, 1744, 1677, 1624, 1579, 1528, 1464, 1368, 1343, 1291, 1270, 1253, 1214, 1162;

$^1$H NMR (80 MHz, CDCl$_3$) δ ppm (TMS): 9.54 (broad d, J=6 Hz, 1H, pyr), 8.47 (broad t, J=7.5 Hz, 1H, pyr), 8.04 (broad t, J=7 Hz, 1H, pyr), 7.85 (broad d, J=8 Hz, 1H, pyr), 5.48 (s, 2H, Pyr-CH$_2$), 5.05 (q, J=7 Hz, 3H, NEt, NH), 4.47 (t, J=6.2 Hz, 2H, COOCH$_2$), 4.16 (t, J=6.5 Hz, 2H, COOCH$_2$), 3.2–2.6 (m, 6H, RCH$_2$N, CH$_2$SCH$_2$), 2.67 (s, 3H, CH$_3$), 1.72 (t, J=7 Hz, 3H, NEt), 1.7–0.7 (m, 29H aprox.).

Analysis calcd. for C$_{31}$H$_{54}$IN$_3$O$_5$S.½H$_2$O: C 50.67%; H 7.82%; N 5.71%. Found: C 50.33%; H 7.65%; N 5.33%.

EXAMPLE 38

2-(N-((2-(2-(3-Phenylpropylcarbamoyloxy)ethoxy)ethoxy)carbonyl) aminomethyl) pyridine Following the procedure described in example 1, but using the product obtained in preparation 10, instead of the one obtained in preparation 1, the title compound was obtained in a similar yield.

IR (film) $\nu_{max}$ (cm$^{-1}$): 3327, 3056, 3021, 2940, 1702, 1591, 1530, 1472, 1449, 1434, 1352, 1256, 1127, 1091, 1048;

$^1$H NMR (80 MHz, CDCl$_3$) δ ppm (TMS): 8.50 (broad t, J=4.5 Hz, 1H, pyr), 7.64 (dt, J$_t$=7.5 Hz, J$_d$=1.8 Hz, 1H, pyr), 7.4–7.0 (m, 7H, C$_6$H$_5$, pyr), 5.9 (broad s, 1H, NH), 4.9 (broad s, 1H, NH), 4.48 (d, J=5.5 Hz, 2H, Pyr-CH$_2$), 4.4–4.1 (m, 4H, COOCH$_2$, COOCH$_2$), 3.8–3.6 (m, 4H, CH$_2$OCH$_2$), 3.18 (q, J=6.3 Hz, 2H, CH$_2$CH$_2$CH$_2$N), 2.64 (t, J=7 Hz, 2H, CH$_2$CH$_2$CH$_2$N), 2.1–1.6 (m, 2H, CH$_2$CH$_2$CH$_2$N).

EXAMPLE 39

2-(N-Acetyl-N-((2-(2-(3-phenylpropylcarbamoyloxy)ethoxy)ethoxy)carbonyl) aminomethyl)pyridine Following the procedure described in example 2, but using the product obtained in example 38, instead of the one obtained in example 1, the title compound was obtained in a similar yield.

IR (film) $\nu_{max}$ (cm$^{-1}$): 3352, 3055, 3020, 2939, 1700, 1590, 1566, 1525, 1472, 1433, 1370, 1338, 1206, 1132, 1080, 1048, 982;

$^1$H NMR (80 MHz, CDCl$_3$) δ ppm (TMS): 8.46 (broad d, J=5 Hz, 1H, pyr), 7.61 (dt, J$_t$=7.5 Hz, J$_d$=1.8 Hz, 1H, pyr), 7.3–7.0 (m, 7H, C$_6$H$_5$, pyr), 5.4 (broad s, 1H, NH), 5.09 (s, 2H, Pyr-CH$_2$), 4.4–4.0 (m, 4H, COOCH$_2$, COOCH$_2$), 3.6–3.3 (m, 4H, CH$_2$OCH$_2$), 3.17 (q, J=6.4 Hz, 2H, CH$_2$CH$_2$CH$_2$N), 2.63 (t, J=7 Hz, 2H, CH$_2$CH$_2$CH$_2$N), 2.60 (s, 3H, CH$_3$), 1.84 (quint, J=7 Hz, 2H, CH$_2$CH$_2$CH$_2$N).

EXAMPLE 40

2-(N-Acetyl-N-((2-(2-(3-phenylpropylcarbamoyloxy)ethoxy)ethoxy)carbonyl) aminomethyl)-1-ethylpyridinium iodide Following the procedure described in example 3, but using the product obtained in example 39, instead of the one obtained in example 2, the title compound was obtained in a similar yield.

IR (film) $\nu_{max}$ (cm$^{-1}$): 3404, 3022, 2935, 1746, 1702, 1624, 1578, 1513, 1446, 1367, 1338, 1213, 1163, 1128, 1087, 1044, 986;

$^1$H NMR (80 MHz, CDCl$_3$) δ ppm (TMS): 9.53 (broad d, J=5 Hz, 1H, pyr), 8.46 (dt, J$_t$=7.5 Hz, J$_d$=1.8 Hz, 1H, pyr), 7.95 (t, J=7 Hz, 1H, pyr), 7.73 (d, J=8 Hz, 1H, pyr), 7.21 (s, 5H, C$_6$H$_5$), 5.43 (s, 2H, Pyr-CH$_2$), 5.05 (q, J=6.3 Hz, 3H, NEt, NH), 4.5–4.3 (m, 2H, COOCH₂), 4.2–4.0 (m, 2H, COOCH₂), 3.8–3.5 (m, 4H, CH₂OCH₂), 3.20 (q, J=7 Hz, 2H, CH₂CH₂CH₂N), 2.64 (t, J=7 Hz, 2H, CH₂CH₂CH₂N), 2.64 (s, 3H, CH₃), 2.0–1.6 (m, 5H, CH₂CH₂CH₂N, NEt).

Analysis calcd. for $C_{25}H_{34}IN_3O_6 \cdot 5/2H_2O$: C 46.59%; H 6.10%; N 6.52%. Found: C 46.68%; H 5.71%; N 6.12%.

EXAMPLE 41

2-(N-((2-(2-(Cyclohexylmethylcarbamoyloxy)ethoxy)ethoxy)carbonyl) aminomethyl)pyridine Following the procedure described in example 1, but using the product obtained in preparation 11, instead of the one obtained in preparation 1, the title compound was obtained in a similar yield.

mp: 65°–67° C.;

IR (KBr) $\nu_{max}$ (cm⁻¹): 3316, 2919, 2848, 1684, 1536, 1471, 1448, 1433, 1256, 1129, 1081, 1053, 1045;

¹H NMR (80 MHz, CDCl₃) δ ppm (TMS): 8.53 (broad d, J=5 Hz, 1H, pyr), 7.67 (dt, $J_t$=7.6 Hz, $J_d$=1.8 Hz, 1H, pyr), 7.3–7.0 (m, 2H, pyr), 5.9 (broad s, 1H, NH), 4.50 (d, J=5.5 Hz, 2H, Pyr-CH₂), 4.4–4.1 (m, 4H, COOCH₂, COOCH₂), 3.8–3.6 (m, 4H, CH₂OCH₂), 3.00 (t, J=6.1 Hz, 2H, chex-CH₂N), 2.0–0.7 (m, 11H, chex).

Analysis calcd. for $C_{19}H_{29}N_3O_5$: C 60.14%; H 7.70%; N 11.07%. Found: C 59.89%; H 7.85%; N 10.82%.

EXAMPLE 42

2-(N-Acetyl-N-((2-(2-(cyclohexylmethylcarbamoyloxy)ethoxy) ethoxy) carbonyl) aminomethyl)pyridine Following the procedure described in example 2, but using the product obtained in example 41, instead of the one obtained in example 1, the title compound was obtained as a colorless oil.

IR (film) $\nu_{max}$ (cm⁻¹): 3348, 2920, 2848, 1750, 1702, 1590, 1566, 1472, 1370, 1339, 1279, 1245, 1207, 1133, 1097, 1079, 983;

¹H NMR (80 MHz, CDCl₃) δ ppm (TMS): 8.50 (broad d, J=5 Hz, 1H, pyr), 7.61 (dt, $J_t$=7.5 Hz, $J_d$=1.8 Hz, 1H, pyr), 7.3–7.0 (m, 2H, pyr), 5.10 (s, 2H, Pyr-CH₂), 5.0 (broad s, 1H, NH), 4.4–4.2 (m, 2H, COOCH₂), 4.2–4.0 (m, 2H, COOCH₂), 3.7–3.4 (m, 4H, CH₂OCH₂), 3.0 (t, J=6.1 Hz, 2H, chex-CH₂), 2.62 (s, 3H, CH₃), 1.7–0.7 (m, 11H, chex).

EXAMPLE 43

2-(N-Acetyl-N-((2-(2-(cyclohexylmethylcarbamoyloxy)ethoxy)ethoxy) carbonyl) aminomethyl)-1-ethylpyridinium iodide Following the procedure described in example 3, but using the product obtained in example 42, instead of the one obtained in example 2, the title compound was obtained as a yellow paste.

IR (film) $\nu_{max}$ (cm⁻¹): 3405 (H₂O), 3146, 2919, 2848, 1747, 1702, 1624, 1579, 1513, 1445, 1367, 1338, 1218, 1162, 1088, 1041, 987;

¹H NMR (80 MHz, CDCl₃) δ ppm (TMS): 9.58 (broad d, J=6 Hz, 1H, pyr), 8.56 (dt, $J_d$=1.8 Hz, $J_t$=7.5 Hz, 1H, pyr), 8.07 (t, J=6.2 Hz, 1H, pyr), 7.85 (broad d, J=8 Hz, 1H, pyr), 5.46 (s, 2H, Pyr-CH₂), 5.05 (q, J=7.3 Hz, 3H, NEt, NH), 4.6–4.3 (m, 2H, COOCH₂), 4.3–4.0 (m, 2H, COOCH₂), 3.9–3.6 (m, 4H, CH₂OCH₂), 2.98 (t, J=6.1 Hz, 2H, chex-CH₂), 2.66 (s, 3H, CH₃), 1.73 (t, J=7.3 Hz, 3H, NEt), 1.9–0.7 (m, 11H, chex).

Analysis calcd. for $C_{23}H_{36}IN_3O_6$: C 47.84%; H 6.28%; N 7.28%. Found: C 47.83%; H 6.43%; N 7.15%.

EXAMPLE 44

2-(N-((2-(2-(2-(Pentadecylcarbamoyloxy)ethoxy)ethoxy)ethoxy) carbonyl) aminomethyl) pyridine Following the procedure described in example 1, but using the product obtained in preparation 12, instead of the one obtained in preparation 1, the title compound was obtained in a similar yield.

mp: 58°–62° C.;

IR (KBr) $\nu_{max}$ (cm⁻¹): 3315, 3060, 2947, 2913, 2844, 1684, 1541, 1485, 1462, 1287, 1140, 1044;

¹H NMR (80 MHz, CDCl₃) δ ppm (TMS): 8.53 (d, J=5 Hz, 1H, pyr), 7.66 (dt, $J_d$=1.8 Hz, $J_t$=7.5 Hz, 1H, pyr), 7.3–7.0 (m, 2H, pyr), 6.0 (broad s, 1H, NH), 4.9 (broad s, 1H, NH), 4.49 (d, J=5.5 Hz, 2H, Pyr-CH₂), 4.4–4.1 (m, 4H, COOCH₂, COOCH₂), 3.8–3.6 (m, 8H, CH₂OCH₂CH₂OCH₂), 3.14 (q, J=6.0 Hz, 2H, RCH₂N), 1.7–0.7 (m, 29H, aprox.).

Analysis calcd. for $C_{29}H_{51}N_3O_6$ C 64.77%; H 9.56%; N 7.81%. Found: C 64.75%; H 9.70%; N 7.66%.

EXAMPLE 45

2-(N-Acetyl-N-((2-(2-(2-(pentadecylcarbamoyloxy) ethoxy) ethoxy) ethoxy) carbonyl) aminomethyl) pyridine Following the procedure described in example 2, but using the product obtained in example 44, instead of the one obtained in example 1, the title compound was obtained in a similar yield.

mp: 42°–43° C.;

IR (KBr) $\nu_{max}$ (cm⁻¹): 3331, 2914, 2846, 1730, 1701, 1684, 1591, 1537, 1463, 1434, 1369, 1340, 1288, 1269, 1253, 1237, 1206, 1135, 1118, 1089;

¹H NMR (80 MHz, CDCl₃) δ ppm (TMS): 8.50 (broad d, J=5 Hz, 1H, pyr), 7.61 (dt, $J_d$=1.8 Hz, $J_t$=7.4 Hz, 1H, pyr), 7.3–7.0 (m, 2H, pyr), 5.09 (s, 2H, Pyr-CH₂), 4.9 (broad s, 1H, NH), 4.4–4.1 (m, 4H, COOCH₂, COOCH₂), 3.7–3.4 (m, 8H, CH₂OCH₂CH₂OCH₂), 3.13 (q, J=6.0 Hz, 2H, RCH₂N), 2.62 (s, 3H, CH₃), 1.7–0.7 (m, 29H aprox.).

Analysis calcd. for $C_{31}H_{53}N_3O_7$: C 64.22%; H 9.21%; N 7.24%. Found: C 63.85%; H 7.06%; N 9.37%.

EXAMPLE 46

2-(N-Acetyl-N-((2-(2-(2-(pentadecylcarbamoyloxy)ethoxy)ethoxy) ethoxy) carbonyl) aminomethyl)-1-ethylpyridinium iodide Following the procedure described in example 3, but using the product obtained in example 45, instead of the one obtained in example 2, the title compound was obtained as a yellow paste.

IR (film) $\nu_{max}$ (cm⁻¹): 3303, 2913, 2846, 1746, 1680, 1624, 1574, 1537, 1445, 1370, 1271, 1236, 1161, 1110, 1086, 1045, 985;

¹H NMR (80 MHz, CDCl₃) δ ppm (TMS): 9.63 (broad d, J=6 Hz, 1H, pyr), 8.53 (dt, $J_d$=1.8 Hz, $J_t$=7.4 Hz, 1H, pyr), 8.07 (broad t, J=6 Hz, 1H, pyr), 7.84 (broad d, J=8 Hz, 1H, pyr), 5.70 (s, 2H, Pyr-CH₂), 5.05 (q, J=7.3 Hz, 3H, NEt, NH), 4.6–4.3 (m, 2H, COOCH₂), 4.3–4.1 (m, 2H, COOCH₂), 3.8–3.5 (m, 8H, CH₂OCH₂CH₂OCH₂), 3.11 (q, J=6.1 Hz, 2H, RCH₂N), 2.66 (s, 3H, CH₃), 1.73 (t, J=7.3 Hz, 3H, NEt), 1.7–0.7 (m, 29H aprox.).

Analysis calcd. for $C_{32}H_{58}IN_3O_7$: C 53.11%; H 8.08%; N 5.80%. Found: C 53.14%; H 7.99%; N 5.59%.

EXAMPLE 47

2-(N-Ethoxycarbonyl-N-((2-(2-(2-(pentadecylcarbamoyloxy)ethoxy) ethoxy) ethoxy) carbonyl) aminomethyl) pyridine Following the procedure described in example 2, but using the product obtained in example 44 and ethyl chlorocarbonate, instead of the one obtained in example 1 and acetyl chloride, respectively, the title compound was obtained in a similar yield.

EXAMPLE 48

2-(N-Ethoxycarbonyl-N-((2-(2-(2-(pentadecylcarbamoyloxy)ethoxy) ethoxy) ethoxy) carbonyl) aminomethyl)-1-ethylpyridinium iodide Following the procedure described in example 3, but using the product obtained in example 47, instead of the one obtained in example 1, the title compound was obtained in a similar yield.

EXAMPLE 49

2-(N-((2-(2-(2-(Heptadecylcarbamoyloxy)ethoxy)ethoxy)ethoxy) carbonyl) aminomethyl) pyridine Following the procedure described in example 1, but using the product obtained in preparation 13, instead of the one obtained in preparation 1, the title compound was obtained in a similar yield.

EXAMPLE 50

2-(N-Acetyl-N-((2-(2-(2-(heptadecylcarbamoyloxy)ethoxy)ethoxy) ethoxy) carbonyl) aminomethyl) pyridine Following the procedure described in example 2, but using the product obtained in example 49, instead of the one obtained in example 1, the title compound was obtained in a similar yield.

EXAMPLE 51

2-(N-Acetyl-N-((2-(2-(2-(heptadecylcarbamoyloxy)ethoxy)ethoxy) ethoxy) carbonyl) aminomethyl)-1-ethylpyridinium iodide Following the procedure described in example 3, but using the product obtained in example 50, instead of the one obtained in example 2, the title compound was obtained in a similar yield.

EXAMPLE 52

2-(N-Ethoxycarbonyl-N-((2-(2-(2-(heptadecylcarbamoyloxy)ethoxy) ethoxy) ethoxy) carbonyl) aminomethyl) pyridine Following the procedure described in example 2, but using the product obtained in example 51 and ethyl chlorocarbonate, instead of the one obtained in example 1 and acetyl chloride, respectively, the title compound was obtained in a similar yield.

EXAMPLE 53

2-(N-Ethoxycarbonyl-N-((2-(2-(2-(heptadecylcarbamoyloxy)ethoxy) ethoxy) ethoxy) carbonyl) aminomethyl)-1-ethylpyridinium iodide Following the procedure described in example 3, but using the product obtained in example 52, instead of the one obtained in example 2, the title compound was obtained in a similar yield.

EXAMPLE 54

2-(N-((2-(2-(2-(2-(Pentadecylcarbamoyloxy)ethoxy)ethoxy)ethoxy) ethoxy) carbonyl) aminomethyl) pyridine Following the procedure described in example 1, but using the product obtained in preparation 14, instead of the one obtained in preparation 1, the title compound was obtained in a similar yield.

EXAMPLE 55

2-(N-Acetyl-N-((2-(2-(2-(2-(pentadecylcarbamoyloxy) ethoxy) ethoxy) ethoxy) ethoxy) carbonyl) aminomethyl)-1-ethylpyridinium iodide Following the procedure described in example 2, but using the product obtained in example 54, instead of the one obtained in example 1, the title compound was obtained in a similar yield.

EXAMPLE 56

2-(N-Acetyl-N-((2-(2-(2-(2-(pentadecylcarbamoyloxy) ethoxy) ethoxy) ethoxy) ethoxy) carbonyl) aminomethyl)-1-ethylpyridinium iodide Following the procedure described in example 3, but using the product obtained in example 55, instead of the one obtained in example 2, the title compound was obtained in a similar yield.

EXAMPLE 57

2-(N-((3-(3-(Heptadecylcarbamoyloxy) propoxy) proxy) carbonyl) aminomethyl) pyridine Following the procedure described in example 1, but using the product obtained in example 15, instead of the one obtained in preparation 1, the title compound was obtained in a similar yield.

EXAMPLE 58

2-(N-Acetyl-N-((3-(3-(heptadecylcarbamoyloxy)-propoxy)propoxy) carbonyl) aminomethyl) pyridine Following the procedure described in example 2, but using the product obtained in example 57, instead of the one obtained in example 1, the title compound was obtained in a similar yield.

EXAMPLE 59

2-(N-Acetyl-N-((3-(3-(heptadecylcarbamoyloxy)-propoxy)propoxy) carbonyl) aminomethyl)-1-ethylpyridinium iodide Following the procedure described in example 3, but using the product obtained in example 58, instead of the one obtained in example 2, the title compound was obtained in a similar yield.

EXAMPLE 60

2-(N-((2-(2-(Heptadecylcarbamoyloxy)ethylthio)ethoxy)carbonyl) aminomethyl) pyridine Following the procedure described in example 1, but using the product obtained in preparation 16, instead of the one obtained in preparation 1, the title compound was obtained in a similar yield.

mp 73°–74° C.;

IR (KBr) $\nu_{max}$ (cm$^{-1}$): 3303, 3052, 2912, 2843, 1680, 1588, 1538, 1462, 1428, 1289, 1274, 1206, 1146, 1073, 1046, 1034, 982;

¹H NMR (80 MHz, CDCl₃) δ ppm (TMS): 8.53 (broad d, J=5 Hz, 1H, pyr), 7.65 (broad t, J=7.5 Hz, 1H, pyr), 7.3-7.0 (m, 2H, pyr), 6.1 (broad s, 1H, NH), 5.0 (broad s, 1H, NH), 4.50 (d, J=5.5 Hz, 2H, Pyr-CH₂), 4.3-4.1 (m, 4H, COOCH₂, COOCH₂), 3.10 (q, J=6.0 Hz, 2H, RCH₂N), 2.79 (t, J=6.5 Hz, 4H, CH₂SCH₂), 1.7-0.7 (m, 33H aprox.).

Analysis calcd. for C₂₉H₅₁N₃O₄S: C 64.76%; H 9.55%; N 7.81%; S 5.96%. Found: C 64.67%; H 9.41%; N 8.08%; S 5.86%.

EXAMPLE 61

2-(N-Acetyl-N-((2-(2-(heptadecylcarbamoyloxy)ethylthio)ethoxy) carbonyl) aminomethyl) pyridine Following the procedure described in example 2, but using the product obtained in example 60, instead of the one obtained in example 1, the title compound was obtained in a similar yield.

mp 62°-63° C.;

IR (KBr) ν$_{max}$ (cm⁻¹): 3325, 2915, 2846, 1740, 1685, 1590, 1529, 1464, 1423, 1384, 1372, 1351, 1260, 1246, 1204, 1141, 1079;

¹H NMR (80 MHz, CDCl₃) δ ppm (TMS): 8.50 (broad d, J=4 Hz, 1H, pyr), 7.60 (dt, J$_t$=1.8 Hz, J$_d$=7.4 Hz, 1H, pyr), 7.3-7.0 (m, 2H, pyr), 5.08 (s, 2H, Pyr-CH₂), 4.9 (broad s, 1H, NH), 4.30 (t, J=7 Hz, 2H, COOCH₂), 4.16 (t, J=4.7 Hz, 2H, COOCH₂), 3.14 (q, J=6 Hz, 2H, RCH₂N), 2.68 (t, J=6.7 Hz, 4H, CH₂SCH₂), 2.62 (s, 3H, CH₃), 1.7-0.7 (m, 33H aprox.).

Analysis calcd. for C₃₁H₅₃N₃O₅S: C 64.21%; H 9.21%; N 7.25%; S 5.53%. Found: C 64.05%; H 9.56%; N 7.37%; S 5.91%.

EXAMPLE 62

2-(N-Acetyl-N-((2-(2-(heptadecylcarbamoyloxy)ethylthio)ethoxy) carbonyl) aminomethyl)-1-ethylpyridinium iodide Following the procedure described in example 3, but using the product obtained in example 61, instead of the one obtained in example 2, the title compound was obtained in a similar yield.

mp: 48°-53° C.;

IR (KBr) ν$_{max}$ (cm⁻¹): 3322, 2912, 2845, 1744, 1686, 1623, 1578, 1508, 1462, 1371, 1338, 1224, 1159;

¹H NMR (80 MHz, CDCl₃) δ ppm (TMS): 9.54 (broad d, J=6 Hz, 1H, pyr), 8.47 (broad t, J=7.5 Hz, 1H, pyr), 8.04 (broad t, J=7 Hz, 1H, pyr), 7.85 (broad d, J=8 Hz, 1H, pyr), 5.50 (s, 2H, Pyr-CH₂), 5.50 (q, J=7 Hz, 3H, NEt, NH), 4.47 (t, J=6.2 Hz, 2H, COOCH₂), 4.16 (t, J=6.5 Hz, 2H, COOCH₂), 3.2-2.6 (m, 6H, RCH₂N, CH₂SCH₂), 2.67 (s, 3H, CH₃), 1.72 (t, J=7 Hz, 3H, NEt), 1.7-0.7 (m, 33H aprox.).

Analysis calcd. for C₃₃H₅₈IN₃O₅S.H₂O: C 52.58%; H 8.02%; N 5.57%. Found: C 52.39%; H 7.84%; N 5.55%.

EXAMPLE 63

2-(N-Acetyl-N-((2-(2-(heptadecylcarbamoyloxy)ethylthio)ethoxy) carbonyl)aminomethyl)-1-ethylpyridinium chloride A solution of the compound obtained in example 62 (3 g, 3.97 mmol) in 70% aqueous methanol was eluted through an ionic interchange column IRA-410 (chloride form). The filtrate was concentrated to dryness and recrystallized in ether: acetone to give the desired compound as a white powder (2.25 g, 88%)

mp: 48°-49° C.;

IR (KBr) ν$_{max}$ (cm⁻¹): 3403, 2913, 2845, 1744, 1692, 1624, 1579, 1524, 1462, 1372, 1362, 1338, 1291, 1253, 1222, 1159, 1089, 987;

¹H NMR (80 MHz, CDCl₃) δ ppm (TMS): 9.97 (broad d, J=6 Hz, 1H, pyr), 8.55 (broad t, J=7.5 Hz, 1H, pyr), 8.08 (broad t, J=7 Hz, 1H, pyr), 7.80 (broad d, J=8 Hz, 1H, pyr), 5.52 (s, 2H, Pyr-CH₂), 5.17 (q, J=7 Hz, 3H, NEt, NH), 4.45 (t, J=6.2 Hz, 2H, COOCH₂), 4.14 (t, J=6.5 Hz, 2H, COOCH₂), 3.2-2.6 (m, 6H, RCH₂N, CH₂SCH₂), 2.67 (s, 3H, CH₃), 1.72 (t, J=7 Hz, 3H, NEt), 1.7-0.7 (m, 33H aprox.).

Analysis calcd. for C₃₃H₅₈ClN₃O₅S.H₂O: C 59.84%; H 9.13%; N 6.34%. Found: C 59.60%; H 9.29%; N 6.28%.

EXAMPLE 64

2-(N-((2-(2-Hexadecyloxyethylthio)ethoxy)carbonyl)aminomethyl) pyridine

Following the procedure described in example 1, but using the product obtained in preparation 17, instead of the one obtained in preparation 1, the title compound was obtained in a similar yield.

mp 55°-56° C.;

IR (KBr) ν$_{max}$ (cm⁻¹): 3310, 3056, 2913, 2845, 1686, 1588, 1542, 1468, 1459, 1424, 1359, 1280, 1153, 1069, 1043, 986;

¹H NMR (80 MHz, CDCl₃) δ ppm (TMS): 8.53 (broad d, J=5 Hz, 1H, pyr), 7.65 (dt, J$_d$=1.8 Hz, J$_t$=7.5 Hz, 1H, pyr), 7.3-7.0 (m, 2H, pyr), 5.8 (broad s, 1H, NH), 4.49 (d, J=5.5 Hz, 2H, Pyr-CH₂), 4.25 (t, J=6.5 Hz, 2H, COOCH₂), 3.59 (t, J=6.5 Hz, 2H, CH₂O), 3.42 (t, J=6.5 Hz, 2H, CH₂O), 2.80 (t, J=6.2 Hz, 2H, CH₂S), 2.72 (t, J=6,2 Hz, 2H, CH₂S), 1.7-0.7 (m, 31H aprox.).

Analysis calcd. for C₂₇H₄₈N₂O₃S: C 67.46%; H 10.06%; N 5.83%; S 6.67%. Found: C 67.24%; H 10.41%; N 5.60%; S 6.93%.

EXAMPLE 65

2-(N-Acetyl-N-((2-(2-hexadecyloxyethylthio)ethoxy)carbonyl) aminomethyl) pyridine Following the procedure described in example 2, but using the product obtained in example 64, instead of the one obtained in example 1, the title compound was obtained in a similar yield.

mp 41°-44° C.;

IR (KBr) ν$_{max}$ (cm⁻¹): 3441, 2914, 2845, 1730, 1698, 1592, 1566, 1477, 1461, 1427, 1382, 1371, 1349, 1290, 1207, 1156, 1107, 1076, 985;

¹H NMR (80 MHz, CDCl₃) δ ppm (TMS): 8.50 (broad d, J=4 Hz, 1H, pyr), 7.59 (dt, J$_t$=1.8 Hz, J$_d$=7.4 Hz, 1H, pyr), 7.3-7.0 (m, 2H, pyr), 5.08 (s, 2H, Pyr-CH₂), 4.29 (t, J=7 Hz, 2H, COOCH₂), 3.53 (t, J=6.6 Hz, 2H, CH₂O), 3.40 (t, J=6.3 Hz, 2H, CH₂O), 2.69 (t, J=6.7 Hz, 2H, CH₂S), 2.64 (t, J=6.7 Hz, 2H, CH₂S), 2.62 (s, 3H, CH₃), 1.7-0.7 (m, 31H aprox.).

Analysis calcd. for C₂₉H₅₀N₂O₄S: C 66.63%; H 9.64%; N 5.36%; S 6.13%. Found: C 66.43%; H 10.08%; N 5.15%; S 6.37%.

EXAMPLE 66

2-(N-Acetyl-N-((2-(2-hexadecyloxyethylthio)ethoxy)carbonyl) aminomethyl)-1-ethylpyridinium iodide Following the procedure described in example 3, but using the product obtained in example 65, instead of the one obtained in example 2, the title compound was obtained in a similar yield.

mp: 59°–74° C.;

IR (KBr) $\nu_{max}$ (cm$^{-1}$): 2916, 2844, 1739, 1692, 1622, 1573, 1507, 1483, 1463, 1445, 1410, 1379, 1369, 1348, 1291, 1277, 1212, 1165, 1107, 1088, 986;

$^1$H NMR (80 MHz, CDCl$_3$) δ ppm (TMS): 9.68 (broad d, J=6 Hz, 1H, pyr), 8.40 (dt, $J_d$=1.8 Hz, $J_t$=7.5 Hz, 1H, pyr), 8.06 (broad t, J=7 Hz, 1H, pyr), 7.80 (broad d, J=8 Hz, 1H, pyr), 5.47 (s, 2H, Pyr-CH$_2$), 5.08 (q, J=7 Hz, 2H, NEt), 4.48 (t, J=6.2 Hz, 2H, COOCH$_2$), 3.58 (t, J=6.5 Hz, 2H, CH$_2$O), 3.42 (t, J=6.2 Hz, 2H, CH$_2$O), 2.92 (t, J=6.3 Hz, 2H, CH$_2$S) 2.69 (t, J=6.1 Hz, 2H, CH$_2$S), 2.67 (s, 3H, CH$_3$), 1.72 (t, J=7 Hz, 3H, NEt), 1.7–0.7 (m, 31H aprox.).

Analysis calcd. for C$_{31}$H$_{55}$IN$_2$O$_4$S: C 54.86%; H 8.17%; N 4.13%. Found: C 54.85%; H 8.42%; N 3.59%.

EXAMPLE 67

2-(N-((2-(2-Octadecyloxyethylthio)ethoxy)carbonyl)aminomethyl) pyridine

Following the procedure described in example 1, but using the product obtained in preparation 18, instead of the one obtained in preparation 1, the title compound was obtained in a similar yield.

mp 60°–62° C.;

IR (KBr) $\nu_{max}$ (cm$^{-1}$): 3311, 3056, 2913, 2845, 1685, 1588, 1546, 1468, 1459, 1424, 1357, 1281, 1153, 1069, 1036, 989;

$^1$H NMR (80 MHz, CDCl$_3$) δ ppm (TMS): 8.53 (broad d, J=5 Hz, 1H, pyr), 7.65 (dt, $J_d$=1.8 Hz, $J_t$=7.5 Hz, 1H, pyr), 7.3–7.0 (m, 2H, pyr), 5.8 (broad s, 1H, NH), 4.49 (d, J=5.5 Hz, 2H, Pyr-CH$_2$), 4.25 (t, J=6.5 Hz, 2H, COOCH$_2$), 3.59 (t, J=6.5 Hz, 2H, CH$_2$O), 3.42 (t, J=6.5 Hz, 2H, CH$_2$O), 2.80 (t, J=6.2 Hz, 2H, CH$_2$S), 2.72 (t, J=6.2 Hz, 2H, CH$_2$S), 1.7–0.7 (m, 35H aprox.).

Analysis calcd. for C$_{29}$H$_{52}$N$_2$O$_3$S: C 68.46%; H 10.30%; N 5.50%; S 6.30%. Found: C 68.29%; H 10.81%; N 5.32%; S 6.94%.

EXAMPLE 68

2-(N-Acetyl-N-((2-(2-octadecyloxyethylthio)ethoxy)carbonyl) aminomethyl) pyridine Following the procedure described in example 2, but using the product obtained in example 67, instead of the one obtained in example 1, the title compound was obtained in a similar yield.

mp 47°–49° C.;

IR (KBr) $\nu_{max}$ (cm$^{-1}$): 3324, 2914, 2845, 1729, 1698, 1592, 1566, 1477, 1461, 1427, 1382, 1371, 1349, 1290, 1208, 1158, 1108, 1076, 985;

$^1$H NMR (80 MHz, CDCl$_3$) δ ppm (TMS): 8.50 (broad d, J=4 Hz, 1H, pyr), 7.59 (dt, $J_t$=1.8 Hz, $J_d$=7.4 Hz, 1H, pyr), 7.3–7.0 (m, 2H, pyr), 5.08 (s, 2H, Pyr-CH$_2$), 4.29 (t, J=7 Hz, 2H, COOCH$_2$), 3.53 (t, J=6.6 Hz, 2H, CH$_2$O), 3.40 (t, J=6.3 Hz, 2H, CH$_2$O), 2.69 (t, J=6.7 Hz, 2H, CH$_2$S), 2.64 (t, J=6.7 Hz, 2H, CH$_2$S), 2.62 (s, 3H, CH$_3$), 1.7–0.7 (m, 35H aprox.).

Analysis calcd. for C$_{31}$H$_{54}$N$_2$O$_4$S: C 67.60%; H 9.88%; N 5.09%; S 5.82%. Found: C 66.83%; H 10.57%; N 5.23%; S 5.94%.

EXAMPLE 69

2-(N-Acetyl-N-((2-(2-octadecyloxyethylthio)ethoxy)carbonyl) aminomethyl)-1-ethylpyridinium idodide Following the procedure described in example 3, but using the product obtained in example 68, instead of the one obtained in example 2, the title compound was obtained in a similar yield.

mp: 41°–53° C.;

IR (KBr) $\nu_{max}$ (cm$^{-1}$): 3445, 2913, 2845, 1743, 1679, 1624, 1578, 1508, 1462, 1427, 1368, 1339, 1292, 1212, 1161, 1114, 987;

$^1$H NMR (80 MHz, CDCl$_3$) δ ppm (TMS): 9.68 (broad d, J=6 Hz, 1H, pyr), 8.40 (dt, $J_d$=1.8 Hz, $J_t$=7.5 Hz, 1H, pyr), 8.06 (broad t, J=7 Hz, 1H, pyr), 7.80 (broad d, J=8 Hz, 1H, pyr), 5.47 (s, 2H, Pyr-CH$_2$), 5.08 (q, J=7 Hz, 2H, NEt), 4.48 (t, J=6.2 Hz, 2H, COOCH$_2$), 3.58 (t, J=6.5 Hz, 2H, CH$_2$O), 3.42 (t, J=6.2 Hz, 2H, CH$_2$O), 2.92 (t, J=6.3 Hz, 2H, CH$_2$S), 2.69 (t, J=6.1 Hz, 2H, CH$_2$S), 2.67 (s, 3H, CH$_3$), 1.72 (t, J=7 Hz, 3H, NEt), 1.7–0.7 (m, 31H aprox.).

Analysis calcd. for C$_{33}$H$_{59}$IN$_2$O$_4$S.H$_2$O: C 54.68%; H 8.48%; N 3.86%. Found: C 54.68%; H 8.53%; N 3.32%.

In the following Formulations are described the preparation of a number of pharmaceutical formulations in accordance with the invention.

FORMULATION 1

Capsules

A well blended mixture of 100 mg of powdery active compound, 197 mg of lactose, and 3 mg of magnesium stearate is encapsulated in a hard gelatin capsule which is washed and dried.

FORMULATION 2

Tablets

A mixture of 100 mg of the active compound, 2.5 mg of magnesium stearate, 125 mg of dibasic calcium phosphate, 10 mg of sodium starch glycolate and 12.5 mg of talc is compounded and tableted.

FORMULATION 3

Injectable Solutions 100 mg of the active compound is mixed with 0.05 ml of benzylic alcohol and 1 ml of propylene glycol. The mixture is made up with sterilized water and then sterilized.

FORMULATION 4

Creams 5 g parts of a base cream is prepared from 40% white petrolatum, 10% lanolin, 5% Span 20, 0.3% Tween 20 and 41.7% water, with which 100 mg of a powdery active compound are admixed.

FORMULATION 5

Coating Liquids 1 part by weight of the active compound is mixed with 99 parts by weight of polyethylene glycol 300.

FORMULATION 6

Ointments 2 parts of the active compound, 40 parts of polyethylene glycol 400 and 58 parts by weight of polyethylene glycol 1500 are mixed and solubilized, with heating, and then cooled.

FORMULATION 7

Aerosol 4 g of the active compound is mixed with 100 ml of propylenglycol and 0.2 g of an aromatizer. The mixture is made up with a suitable propellant.

FORMULATION 8

Syrup 0.4 g of the active substance are mixed with 45 g of sacharose, 0.2 g of an aromatizer and 0.1 g of sodium saccharine. The mixture is made up with water to 100 ml.

The compounds of the present invention have valuable PAF antagonist activity, which may be used both for the treatment and protection of animals, including human beings, as illustrated by the following Experiments:

EXPERIMENT 1

Inhibition of Platelet Aggregation Induced by PAF

The blood is obtained by cardiac puncture of male New Zealand albino rabbits (between 2 and 2.5 Kg of weight) and coagulation is prevented by adding 1 part of 3.16% sodium citrate dihydrate in 9 parts of blood. The platelet rich plasma (PRP) is prepared by blood centrifugation at 250×g for 10 min. at 4° C. and it is diluted with platelet poor plasma (PPP) by additional centrifugation at 3000×g for 10 min. The amount of platelets is adjusted to $3 \times 10^{-5}/mm^3$. the platelet aggregation induced by PAF ($C_{18}$; prepared in our laboratory) (16 nM, final) is determined by the Born nephelometric technique (J. Physiol., 1962, 162, 67) using a aggregometer Chrono-log 500. The activities of the inhibitors are expressed as IC$_{50}$, that is to say the concentration of the drug needed to inhibit the platelet aggregation by 50%. The results are shown in table 1:

TABLE 1

| Compound number | IC$_{50}$ (μM) |
|---|---|
| 3 | 0.019 |
| 9 | 1.5 |
| 12 | 0.027 |
| 13 | 1.6 |
| 14 | 0.054 |
| 16 | 0.012 |
| 19 | 0.019 |
| 20 | 0.22 |
| 22 | 0.027 |
| 25 | 0.051 |
| 31 | 0.032 |
| 37 | 0.0068 |
| 40 | 1.2 |
| 43 | 2.0 |
| 46 | 0.012 |
| 62 | 0.0044 |
| 63 | 0.012 |
| 66 | 0.0044 |
| 69 | 0.015 |

EXPERIMENT 2

Inhibition of the Hypotensive Effect Induced by PAF in Normotense Rats

Male Sprage Dawley rats, of 180-220 g of weight, anesthetized with sodium pentobarbital (50 mg/Kg, i.p. 1 mL/100 g) have been used. In order to measure the average arterial pressure, a polyethylene catheter is introduced into the carotid artery. The arterial pressure is recorded with the help of a transducer connected with a R611 Beckman polygraph. The tested compounds are administered through the femoral vein 3 min before the injection of PAF (0.5 mcg/Kg, i.v.). The inhibition of the hypotension induced by PAf of the different compounds expressed as IC$_{50}$, is shown in table 2.

TABLE 2

| Compound number | CI$_{50}$ (mg/Kg, i.v.) |
|---|---|
| 3 | 0.022 |
| 9 | 5.0 |
| 12 | 0.067 |
| 13 | 0.5 |
| 14 | 0.13 |
| 16 | 0.021 |
| 19 | 0.041 |
| 20 | 0.68 |
| 22 | 0.032 |
| 25 | 0.064 |
| 31 | 0.057 |
| 37 | 0.044 |
| 40 | 0.88 |
| 43 | 0.5 |
| 46 | 0.028 |
| 62 | 0.013 |
| 63 | 0.018 |
| 66 | 0.014 |
| 69 | 0.016 |

We claim:

1. A compound having the following formula (I)

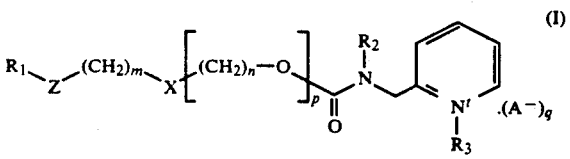

in which:

R$_1$ represents a C$_{10}$-C$_{24}$ alkyl, alkenyl or alkynyl group, a tert-butyl group, an aryl-C$_1$-C$_{12}$ alkyl group or a cyclohexyl-C$_1$-C$_{12}$-alkyl group;

R$_2$ is hydrogen or a —C(=O)R$_4$ group, wherein R$_4$ represents C$_1$-C$_6$ alkyl or C$_1$-C$_6$ alkoxide;

Z is —NR$_5$C(=O)O—, wherein R$_5$ is hydrogen, C$_1$-C$_4$ alkyl, or C$_1$-C$_4$ acyl;

X is —O— or —S—;

m and n are 2, 3, 4, 5, or 6 indpendently;

p is 1;

q is 0 or 1;

t is (+) when q=1, and t has no meaning when q=0;

R$_3$ is hydrogen or C$_1$-C$_6$ alkyl when q=1 and it is an electron pair when q=0;

A— is a phamaceutically acceptable ion.

2. A compound as claimed in claim 1, wherein:

R$_1$ represents a C$_{10}$-C$_{24}$ alkyl group, a tert-butyl group, an aryl-C$_1$-C$_6$ alkyl group or a cyclohexyl-C$_1$-C$_6$-alkyl group;

R$_2$ is hydrogen or a —C(=O)R$_4$ group, wherein R$_4$ represents a C$_1$-C$_3$ alkyl or C$_1$-C$_3$ alkoxide;

Z is —NR$_5$C(=O)O—, wherein R$_5$ hydrogen, C$_1$-C$_4$ alkyl, or C$_1$-C$_4$ acyl;

X is —O— or —S—;

m and n are 2 or 3 indpendently;

p is 1;

q is 0 or 1;

t is (+) when q=1, and t has no meaning when q=0;

$R_3$ is hydrogen or $C_1$-$C_3$ alkyl when q=1 and it is an electron pair when q=0;

A— is a pharmaceutically acceptable ion.

3. A compound claimed in claim 2, wherein:
$R_1$ represents a $C_{10}$-$C_{20}$ alkyl group, a tert-butyl group, a 3-phenylpropyl group or a cyclohexylmethyl group;
$R_2$ is a —C(=O)$R_4$ group, wherein $R_4$ represents a $C_1$-$C_3$ alkyl group;
Z is —NHC(=O)O—;
X is —O—;
m and n are 2 or 3 independently;
p is 1;
q is 1;
t is (+);
$R_3$ ethyl or propyl;
A— is iodide or chloride.

4. A compound as claimed in claim 2, wherein:
$R_1$ represents a $C_{10}$-$C_{20}$ alkyl group, a tert-butyl group, a 3-phenylpropyl group or a cyclohexylmethyl group;
$R_2$ is a —C(=O)$R_4$ group, wherein $R_4$ represents a $C_1$-$C_3$ alkyl group;
Z is —NHC(=O)O—;
X is —S—;
m and n are 2 or 3 independently;
p is 1;
q is 1;
t is (+);
$R_3$ is ethyl or propyl;
A— is iodide or chloride.

5. A compound claimed in claim 3, wherein:
$R_1$ represents a $C_{10}$-$C_{20}$ alkyl group;
$R_2$ is a —C(=O)CH$_3$ group;
m and n are 2;
$R_3$ is ethyl;
Z, X, p, q, t, and A— are as defined in claim 3.

6. A compound as claimed in claim 4, wherein:
$R_1$ represents a $C_{10}$-$C_{20}$ alkyl group;
$R_2$ is a —C(=O)CH$_3$ group;
m and n are 2;
$R_3$ is ethyl;
Z, X, p, q, t, and A— are as defined in claim 4.

7. A compound as claimed in claim 6, wherein:
$R_1$ represents a $C_{15}$-$C_{17}$ alkyl group;
Z is —NHC(=O)O—;
$R_2$, $R_3$, X, m, n, p, q, t, and A— are as defined in claim 6.

8. 2-(N-acetyl-N-((2-(2-pentadecylcarbamoyloxy)ethoxy)ethoxy)carbonyl)aminomethyl)-1-ethyl-pryridinium iodide.

9. 2-(N-acetyl-N-((5-(pentadecylcarbamoyloxy)pentoxy)carbonyl)aminomethyl)-1-ethylpyridinium iodide.

10. 2-(N-acetyl-N-((2-(2-pentadecylcarbamoyloxy)ethylthio)ethoxy)carbonyl)aminomethyl)-1-ethyl-pyridinium iodide.

11. 2-(N-acetyl-N-((2-(2-(2-(pentadecylcarbamoyloxy)ethoxy)ethoxy)ethoxy)carbonyl)aminomethyl)-1-ethylpyridinium iodide.

12. 2-(N-acetyl-N-((2-(2-heptadecylcarbamoyloxy)ethylthio)ethoxy)carbonyl)aminomethyl)-1-ethyl-pyridinium iodide.

13. 2-(N-acetyl-N-((2-(2-heptadecylcarbamoyloxy)ethylthio)ethoxy)carbonyl)aminomethyl)-1-ethyl-pyridinium chloride.

14. A pharmaceeutical composition comprising a pharmaceutically acceptable carrier or diluent in admixture with an effective amount of a compound of formula (I)

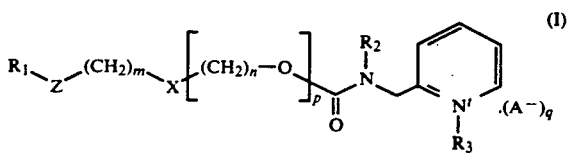

in which:
$R_1$ represents a $C_{10}$-$C_{24}$ alkyl, alkenyl or alkynyl group, a tert-butyl group, an aryl-$C_1$-$C_{12}$ alkyl group or a cyclohexyl-$C_1$-$C_{12}$-alkyl group;
$R_2$ is hydrogen or a —C(=O)$R_4$ group, wherein $R_4$ represents $C_1$-$C_6$ alkyl or $C_1$-$C_6$ alkoxide;
Z is —NR$_5$C(=O)O—, wherein $R_5$ is hydrogen, $C_1$-$C_4$ alkyl, or $C_1$-$C_4$ acyl;
X is —O— or —S—;
m and n are 2, 3, 4, 5, or 6 independently;
p is 1;
q is 0 or 1;
t is (+) when q=1, and t has no meaning when q=0;
$R_3$ is hydrogen or $C_1$-$C_6$ alkyl when q=1 and it is an electron pair when q=0;
A— is a pharmaceutically acceptable ion.

15. A composition according to claim 14 in which
$R_1$ represents a $C_{10}$-$C_{20}$ alkyl group, a tert-butyl group, a 3-phenylpropyl group or a cyclohexylmethyl group;
$R_2$ is a —C(=O)$R_4$ group, wherein $R_4$ represents a $C_1$-$C_3$ alkyl group;
Z is —NHC(=O)O—;
X is —O—;
m and n are 2 or 3 independently;
p is 1;
q is 1;
t is (+);
$R_3$ is ethyl or propyl;
A— is iodide or chloride.

16. A composition according to claim 14 in which
$R_1$ represents a $C_{10}$-$C_{20}$ alkyl group, a tert-butyl group, a 3-phenylpropyl group or a cyclohexylmethyl group;
$R_2$ is a —C(=O)$R_4$ group, wherein $R_4$ represents a $C_1$-$C_3$ alkyl group;
Z is —NHC(=O)O—;
X is —S—;
m and n are 2 or 3 independently;
p is 1;
q is 1;
t is (+);
$R_3$ is ethyl or propyl;
A— is iodide or chloride.

17. A method for treating a patient suffering from a PAF-mediated illness which comprises administering to said patient an effective dose of a composition according to claim 14.

18. A method according to claim 14 which comprises administering to said patient an effective dose of a composition according to claim 15.

19. A method according to claim 17 which comprises administering to said patient an effective dose of a composition according to claim 16.